(12) United States Patent
Ikenaga et al.

(10) Patent No.: US 10,570,498 B2
(45) Date of Patent: Feb. 25, 2020

(54) MANUFACTURING METHOD FOR DEPOSITION MASK, METAL PLATE USED FOR PRODUCING DEPOSITION MASK, AND MANUFACTURING METHOD FOR SAID METAL SHEET

(71) Applicant: Dai Nippon Printing Co., Ltd., Tokyo (JP)

(72) Inventors: Chikao Ikenaga, Tokyo (JP); Hiroaki Nakayama, Tokyo (JP); Kazunari Ikeda, Tokyo (JP); Chiaki Hatsuta, Tokyo (JP); Utako Oouchi, Tokyo (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 0 days.

(21) Appl. No.: 15/548,897
(22) PCT Filed: Feb. 5, 2016
(86) PCT No.: PCT/JP2016/053580
§ 371 (c)(1),
(2) Date: Aug. 4, 2017
(87) PCT Pub. No.: WO2016/129533
PCT Pub. Date: Aug. 18, 2016

(65) Prior Publication Data
US 2018/0023182 A1 Jan. 25, 2018

(30) Foreign Application Priority Data
Feb. 10, 2015 (JP) .................................. 2015-024617

(51) Int. Cl.
*H01L 51/56* (2006.01)
*C23C 14/04* (2006.01)
(Continued)

(52) U.S. Cl.
CPC .............. *C23C 14/042* (2013.01); *C21D 1/74* (2013.01); *C21D 6/001* (2013.01); *C22C 38/08* (2013.01);
(Continued)

(58) Field of Classification Search
CPC ......... C23C 14/042; C23C 14/58; C23F 1/28; C23F 1/02; C23F 1/00; C22C 38/40;
(Continued)

(56) References Cited

U.S. PATENT DOCUMENTS 1,517,633 A   12/1924   Junkers
4,494,205 A    1/1985   Dairiki et al.
(Continued)

FOREIGN PATENT DOCUMENTS

CN   1255168 A   5/2000
CN   1295334 A   5/2001
(Continued)

OTHER PUBLICATIONS

Machine Translation of JP-2000256800-A, Sep. 2000 (Year: 2000).*
(Continued)

*Primary Examiner* — Jun S Yoo
(74) *Attorney, Agent, or Firm* — Burr & Brown, PLLC

(57) ABSTRACT

The present invention provides a metal sheet, on a first surface of which a resist pattern having a narrow width can be stably provided. This manufacturing method for a metal sheet includes a preparation step of preparing a sheet material comprising an iron alloy that contains nickel. When a composition analysis of the first surface of the metal sheet obtained from the sheet material is performed using X-ray photoelectron spectroscopy, the ratio A1/A2 obtained by the result of the X-ray photoelectron spectroscopy does not exceed 0.4, where A1 is the sum of the peak area value of nickel oxide and the peak area value of nickel hydroxide, and A2 is the sum of the peak area value of iron oxide and the peak area value of iron hydroxide.

11 Claims, 24 Drawing Sheets

(51) Int. Cl.

| | | |
|---|---|---|
| *C23F 1/00* | (2006.01) | |
| *H05B 33/10* | (2006.01) | |
| *C23C 14/58* | (2006.01) | |
| *C21D 1/74* | (2006.01) | |
| *C21D 6/00* | (2006.01) | |
| *C22C 38/08* | (2006.01) | |
| *C22C 38/40* | (2006.01) | |
| *C23F 1/02* | (2006.01) | |
| *C23F 1/28* | (2006.01) | |
| *H01L 51/50* | (2006.01) | |
| *H01L 51/00* | (2006.01) | |

(52) U.S. Cl.
CPC .............. *C22C 38/40* (2013.01); *C23C 14/04* (2013.01); *C23C 14/58* (2013.01); *C23F 1/00* (2013.01); *C23F 1/02* (2013.01); *C23F 1/28* (2013.01); *H01L 51/50* (2013.01); *H01L 51/56* (2013.01); *H05B 33/10* (2013.01); *H01L 51/0011* (2013.01)

(58) Field of Classification Search
CPC .......... C22C 38/08; C21D 6/001; C21D 1/74; H05B 33/10; H01L 51/0011; H01L 51/56
See application file for complete search history.

(56) References Cited

U.S. PATENT DOCUMENTS

| | | | |
|---|---|---|---|
| 4,528,246 A | 7/1985 | Higashinakagawa et al. | |
| 4,596,943 A * | 6/1986 | Akiyoshi ................ | H01J 9/142 313/402 |
| 5,200,025 A | 4/1993 | Toei et al. | |
| 6,316,869 B1 | 11/2001 | Kim et al. | |
| 6,423,160 B1 | 7/2002 | Arimoto et al. | |
| 6,559,583 B1 | 5/2003 | Kanayama et al. | |
| 6,875,542 B2 | 4/2005 | Yotsuya | |
| 7,648,729 B2 | 1/2010 | Nakadate | |
| 8,313,806 B2 | 11/2012 | Matsuura | |
| 8,545,631 B2 | 10/2013 | Kim et al. | |
| 2001/0047839 A1 | 12/2001 | Hatano et al. | |
| 2002/0053865 A1* | 5/2002 | Makita .................... | H01J 29/07 313/402 |
| 2002/0117241 A1 | 8/2002 | Etoh | |
| 2003/0228417 A1 | 12/2003 | Nishikawa et al. | |
| 2004/0135498 A1 | 7/2004 | Takanosu et al. | |
| 2004/0142202 A1 | 7/2004 | Kinoshita et al. | |
| 2005/0034810 A1 | 2/2005 | Yamazaki et al. | |
| 2005/0170075 A1 | 8/2005 | Chung | |
| 2006/0103289 A1 | 5/2006 | Kim et al. | |
| 2007/0017895 A1 | 1/2007 | Yotsuya et al. | |
| 2007/0051439 A1 | 3/2007 | Van Der Winden | |
| 2007/0072337 A1 | 3/2007 | Matsuzaki et al. | |
| 2007/0148490 A1* | 6/2007 | Hasegawa ............ | B23K 1/0012 428/679 |
| 2011/0131792 A1 | 6/2011 | Kwak et al. | |
| 2011/0220493 A1 | 9/2011 | Aratake | |
| 2012/0060756 A1 | 3/2012 | Ookawara et al. | |
| 2015/0037928 A1 | 2/2015 | Hirobe et al. | |
| 2016/0208392 A1 | 7/2016 | Ikenaga et al. | |
| 2016/0237546 A1 | 8/2016 | Ikenaga et al. | |
| 2016/0293472 A1 | 10/2016 | Chang et al. | |
| 2017/0141315 A1 | 5/2017 | Ikenaga | |

FOREIGN PATENT DOCUMENTS

| | | |
|---|---|---|
| CN | 1316016 A | 10/2001 |
| CN | 103205701 A | 7/2003 |
| CN | 1514675 A | 7/2004 |
| CN | 1526850 A | 9/2004 |
| CN | 1621555 A | 6/2005 |
| CN | 1754968 A | 4/2006 |
| CN | 1776525 A | 5/2006 |
| CN | 1901138 A | 1/2007 |
| CN | 101210307 A | 7/2008 |
| CN | 102162082 A | 8/2011 |
| CN | 202786401 U | 3/2013 |
| CN | 103031578 A | 4/2013 |
| EP | 0 055 587 A2 | 7/1982 |
| JP | S56-041331 A1 | 4/1981 |
| JP | H05-009755 A1 | 1/1993 |
| JP | H05-208206 A1 | 8/1993 |
| JP | H06-238384 A1 | 8/1994 |
| JP | H07-227620 A1 | 8/1995 |
| JP | H08-067914 A1 | 3/1996 |
| JP | H09-087741 A1 | 3/1997 |
| JP | H09-095740 A1 | 4/1997 |
| JP | H09-324285 A1 | 12/1997 |
| JP | H10-053858 A1 | 2/1998 |
| JP | H10-060525 A1 | 3/1998 |
| JP | H10-214562 A1 | 8/1998 |
| JP | H11-057812 A1 | 3/1999 |
| JP | H11-229040 A1 | 8/1999 |
| JP | 2000-256800 A1 | 9/2000 |
| JP | 2000256800 A * | 9/2000 |
| JP | 2000-345242 A1 | 12/2000 |
| JP | 2001-226718 A1 | 8/2001 |
| JP | 2001-234385 A1 | 8/2001 |
| JP | 2001-247939 A1 | 9/2001 |
| JP | 2001-325881 A1 | 11/2001 |
| JP | 2002-237254 A1 | 8/2002 |
| JP | 2003-100460 A1 | 4/2003 |
| JP | 2003-272838 A1 | 9/2003 |
| JP | 2003-272839 A1 | 9/2003 |
| JP | 2003-286527 A1 | 10/2003 |
| JP | 2004-039319 A1 | 2/2004 |
| JP | 2004-063375 A1 | 2/2004 |
| JP | 2004-185890 A1 | 7/2004 |
| JP | 2004-362908 A1 | 12/2004 |
| JP | 2005-105406 A1 | 4/2005 |
| JP | 2005-154879 A1 | 6/2005 |
| JP | 2005-183153 A1 | 7/2005 |
| JP | 2005-340138 A1 | 12/2005 |
| JP | 2006-247721 A1 | 9/2006 |
| JP | 2007-095324 A1 | 4/2007 |
| JP | 2008-041553 A1 | 2/2008 |
| JP | 2008-255449 A1 | 10/2008 |
| JP | 2009-019243 A1 | 1/2009 |
| JP | 2009-074160 A1 | 4/2009 |
| JP | 2009-120919 A1 | 6/2009 |
| JP | 2010-216012 A1 | 9/2010 |
| JP | 2011-190509 A1 | 9/2011 |
| JP | 2012-111195 A1 | 6/2012 |
| JP | 2013-016491 A1 | 1/2013 |
| JP | 5382257 B1 | 1/2014 |
| JP | 5382259 B1 | 1/2014 |
| JP | 5455099 B1 | 3/2014 |
| JP | 2014-065928 A1 | 4/2014 |
| JP | 5459632 B1 | 4/2014 |
| JP | 5516816 B1 | 6/2014 |
| JP | 2014-148740 A1 | 8/2014 |
| JP | 5626491 B1 | 11/2014 |
| JP | 5641462 B1 | 12/2014 |
| JP | 2015-017308 A1 | 1/2015 |
| KR | 10-2005-0100701 A | 10/2005 |
| KR | 10-2006-0021343 A | 3/2006 |
| KR | 10-0796617 B1 | 1/2008 |
| TW | 201435111 A | 9/2014 |
| WO | 9851833 A1 | 11/1998 |
| WO | 2014/038510 A1 | 3/2014 |

OTHER PUBLICATIONS

English translation of JP2000256800 (Year: 2000).*
English translation of JP2014065928 (Year: 2014).*
English translation of International Preliminary Report on Patentability (Chapter I) (Application No. PCT/JP2016/053580) dated Aug. 24, 2017, 7 pages.
International Search Report and Written Opinion (Application No. PCT/JP2016/053580) dated Apr. 26, 2016.
Japanese Office Action (Application No. 2016-021255) dated Apr. 22, 2016 (with English translation).

(56) References Cited

OTHER PUBLICATIONS

Japanese Office Action (Application No. 2016-021255) dated Aug. 19, 2016 (with English translation).
H. Tohma, "Actual Background Treatment," *Journal of Surface Analysis*, 2001, vol. 8, pp. 49-54.
Japanese Office Action (Application No. 2016-199397) dated Jun. 29, 2018 (with English translation).
Extended European Search Report (Application No. 16749177.8) dated Jul. 19, 2018.
"Selection of Optimum Process of Manufacturing a Nickel Foil by Electrolysis" (Beijing Colored Metal Research Paper), Dec. 31, 1993, pp. 23-26.
Chinese Office Action (Application No. 201680001423.2) dated May 2, 2018 (with English translation).
Chinese Office Action (Application No. 201580024875.8) dated May 24, 2018 (with English translation).
Taiwanese Office Action (Application No. 105104155) dated Apr. 20, 2018.
Extended European Search Report (Application No. 15792096.8) dated May 4, 2018.
Chinese Office Action (Application No. 201711267429.7) dated May 7, 2019 (with English translation).
Written Amendment (Japanese Application No. 2016-021255) dated Jun. 21, 2016 (with English translation).
Japanese Written Opinion (Japanese Application No. 2016-021255) dated Jun. 21, 2016 (with English translation).
Written Amendment (Japanese Application No. 2016-021255) dated Oct. 7, 2016 (with English translation).
Written Opinion (Japanese Application No. 2016-021255) dated Oct. 7, 2016 (with English translation).
Written Statement (Japanese Application No. 2016-199397) dated Feb. 24, 2017 (with English translation).
Written Amendment (Japanese Application No. 2016-199397) dated Jan. 25, 2018 (with English translation).
Written Opinion (Japanese Application No. 2016-199397) dated Jan. 25, 2018 (with English translation).
Written Request for Trial (Japanese Application No. 2016-199397) dated Dec. 28, 2018 (with English translation).
Record of Communication (Japanese Application No. 2016-199397) dated Apr. 10, 2019 (with English translation).
Written Amendment (Japanese Application No. 2016-199397) dated Apr. 9, 2019 (with English translation).
Written Opinion (Japanese Application No. 2016-199397) dated Apr. 9, 2019 (with English translation).
Written Statement (Japanese Application No. 2018-010979) dated Jan. 31, 2018 (with English translation).
Written Amendment (Japanese Application No. 2018-010979) dated Jan. 31, 2018 (with English translation).
Written Amendment (Japanese Application No. 2018-010979) dated Apr. 19, 2019 (with English translation).
Written Opinion (Japanese Application No. 2018-010979) dated Apr. 19, 2019 (with English translation).
Written Amendment (Korean Application No. 20167032510) dated Dec. 7, 2017 (with English translation).
Written Opinion (Korean Application No. 20167032510) dated Dec. 7, 2017 (with English translation).
Written Amendment (Chinese Application No. 201680001423.2) dated Sep. 17, 2018 (with English translation).
Written Opinion (Chinese Application No. 201680001423.2) dated Sep. 17, 2018 (with English translation).
Supplemental (Chinese Application No. 201680001423.2) dated Sep. 17, 2018 (with English translation).
Written Amendment (Chinese Application No. 201680001423.2) dated Dec. 7, 2018 (with English translation).
Written Amendment (Chinese Application No. 201680001423.2) dated Jun. 3, 2019 (with English translation).
Written Opinion (Chinese Application No. 201680001423.2) dated Jun. 3, 2019 (with English translation).
Written Amendment (Taiwan Application No. 105104155) dated Sep. 21, 2018 (with English translation).

Written Opinion (Taiwan Application No. 105104155) dated Sep. 21, 2018 (with English translation).
Written Amendment (Taiwan Application No. 105104155) dated Dec. 7, 2018 (with English translation).
Written Amendment and Written Opinion (EP Application No. 16749177.8) dated Feb. 15, 2019 (with English translation).
Written Amendment and Written Opinion (EP Application No. 16749177.8) dated May 2, 2019 (with English translation).
"Method for Measuring Radius of Curvature of Arc," *Curriculum of Investigation into Dynamics of Traffic Accidents*, Oct. 31, 2002, pp. 378-379 (with English translation).
Hiromu Suzuki, "Shape Control Technology in the Rolling of Metal Strip," *Journal of the Japan Society of Mechanical Engineers*, Jun. 1984, vol. 87, Issue 787, pp. 13-18 (with English translation).
Japanese Office Action (Application No. 2013-190881) dated Nov. 1, 2013 (with English translation).
Japanese Office Action (Application No. 2013-215061) dated Dec. 10, 2013 (with English translation).
Chinese Office Action (Application No. 201480048190.2) dated Feb. 9, 2017 (with English translation).
Chinese Office Action (Application No. 201480056293.3) dated Dec. 21, 2016 (with English translation).
Chinese Office Action (Application No. 201480003438.3) dated Oct. 11, 2016 (with English translation).
Chinese Office Action (Application No. 201480003445.3) dated Oct. 8, 2016 (with English translation).
Korean Office Action (Application No. 10-2015-7009819) dated Oct. 17, 2016 (with English translation).
Korean Office Action (Application No. 10-2015-7009821) dated Oct. 17, 2016 (with English translation).
Korean Office Action (Application No. 10-2016-7006016) dated Nov. 25, 2016 (with English translation).
Korean Office Action (Application No. 10-2016-7009298) dated Oct. 17, 2016 (with English translation).
Korean Office Action (Application No. 10-2016-7031159) dated Nov. 14, 2017 (with English translation).
English translation of International Preliminary Report on Patentability (Application No. PCT/JP2014/050345) dated Jul. 23, 2015.
English translation of International Preliminary Report on Patentability (Application No. PCT/JP2014/050346) dated Jul. 23, 2015.
English translation of International Preliminary Report on Patentability (Application No. PCT/JP2014/074255) dated Mar. 24, 2016.
English translation of International Preliminary Report on Patentability (Application No. PCT/JP2014/075168) dated Apr. 28, 2016.
English translation of International Preliminary Report on Patentability (Application No. PCT/JP2015/062782) dated Nov. 24, 2016.
U.S. Office Action (U.S. Appl. No. 15/026,009) dated Mar. 31, 2017.
Chinese Office Action (Application No. 201711428597.X) dated Jul. 3, 2019 (with English translation).
Marcus P et al: "XPS study of the passive films formed on nitrogen-implanted austenitic stainless steels", Applied Surface Science, Elsevier Amsterdam, NL, vol. 59, No. 1, Jan. 1, 1992 (Jan. 1, 1992), pp. 7-21, XP024640826, ISSN: 0169-4332, DOI: 10.1016/0169-4332(92)90163-R [retrieved on Jan. 1, 1992] *Section 2; p. 8-p. 10*; *Section 3.3; p. 12-p. 13*; * figure 5 *, 15 pages.
Extended European Search Report from a corresponding European patent application (EP 19200746.6) dated Nov. 29, 2019, 13 pages.
Adams D W et al: "High Resolution Solid State Sensor for Strip Edge Drop and Thickness Profile", Aise Steel Technology, Aise, Pittsburgh, PA, US, vol. 75, No. 9, Sep. 1, 1998 (Sep. 1, 1998), pp. 33-36, XP000788068, ISSN: 0021-1559, 4 pages.
Adams D W: "Thickness, Coating Weight And Width Instrumentation", Steel Times, Fuel & Metallurgical Journals Ltd. London, GB, vol. 220, No. 1, Jan. 1, 1992 (Jan. 1, 1992), pp. 10, 12, XP0002461287, ISSN: 0039-095X, 2 pages.
Extended European Search Report from a corresponding European patent application (EP 19196714.0) dated Dec. 13, 2019, 7 pages.
U.S. Office Action from U.S. Appl. No. 15/703,101 dated Dec. 12, 2019, 23 pages.

* cited by examiner

MANUFACTURING METHOD FOR DEPOSITION MASK, METAL PLATE USED FOR PRODUCING DEPOSITION MASK, AND MANUFACTURING METHOD FOR SAID METAL SHEET

TECHNICAL FIELD

The present invention relates to a manufacturing method for a deposition mask with a plurality of through-holes formed therein. In addition, the present invention relates to a method for manufacturing a metal used for producing the deposition mask, and a manufacturing method for the metal sheet.

Background Art

A display device used in a portable device such as a smart phone and a tablet PC is required to have high fineness, e.g., a pixel density of 300 ppi or more. In addition, there is increasing demand that the portable device is applicable in the full high-definitions reference. In this case, the pixel density of the display device needs to be 450 ppi or more, for example.

An organic EL display device draws attention because of its excellent responsibility and low power consumption. A known method for forming pixels of an organic EL display device is a method which uses a deposition mask including through-holes that are arranged in a desired pattern, and forms pixels in the desired pattern. To be specific, a deposition mask is firstly brought into tight contact with a substrate for organic EL display device, and then the substrate and the deposition mask in tight contact therewith are put into a deposition apparatus so as to deposit an organic material and so on.

A deposition mask can be generally manufactured by forming through-holes in a metal plate by etching using photolithographic technique (see, for example, Patent Document 1). For example, a first resist pattern is firstly formed on a first surface of the metal plate, and a second resist pattern is formed on a second surface of the metal plate. Then, an area of the second surface of the metal plate, which is not covered with the second resist pattern, is etched to form second recesses in the second surface of the metal plate. Thereafter, an area of the first surface of the metal plate, which is not covered with the first resist pattern, is etched to form first recesses in the first surface of the metal plate. At this time, by etching the areas such that each first recess and each second recess communicate with each other, through-holes passing through the metal plate can be formed.

In a deposition step using a deposition mask, a deposition mask and a substrate are arranged such that a second surface side of the deposition mask faces the substrate. In addition, a crucible storing a deposition material such as an organic material is arranged on a first surface side of the deposition mask. Then, the deposition material is heated to evaporate or sublimate the deposition material. The evaporated or sublimated deposition material adheres to the substrate through the through-holes in the deposition mask. As a result, the deposition material is deposited on a surface of the substrate, in a desired pattern corresponding to the through-hole positions of the deposition mask.

Patent Document 1: JP2014-148740A

DISCLOSURE OF THE INVENTION

As a pixel density of an organic EL display device increases, a size and an arrangement pitch of through-holes of a deposition mask decrease. When through-holes are formed in a metal plate by etching using the photolithographic technique, a width of resist pattern provided on a first surface or a second surface of the metal plate narrows. Thus, it is required for a resist film for forming a resist pattern to have a high resolution. To make narrower the resist pattern width means that a contact area between the resist pattern and the metal plate is reduced. Thus, it is also required for the resist film for forming a resist pattern to have a high adhesion force to the metal plate.

The present invention has been made in view of the above circumstances. The object of the present invention is to provide a method for manufacturing a metal plate on which surface a resist pattern of a narrow width can be stably provided, and such a metal plate. In addition, the present invention relates to a method for manufacturing a deposition mask using such a metal plate.

The present invention is a manufacturing method for a metal plate used for manufacturing a deposition mask having a plurality of through-holes formed therein, the method comprising a preparation step of preparing a plate member made of an iron alloy containing nickel, wherein: when a composition analysis of a first surface of the metal plate obtained from the plate member is performed by using an X-ray photoelectron spectroscopy, a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide; and in the composition analysis of the first surface of the metal plate by means of the X-ray photoelectron spectroscopy, an incident angle of an X-ray emitted to the metal plate on the first surface is 45 degrees, and an acceptance angle of photoelectrons discharged from the metal plate is 90 degrees.

The manufacturing method for a metal plate according to the present invention may further comprise an annealing step of annealing the plate member to obtain the metal plate.

In the manufacturing method for a metal plate according to the present invention, the annealing step may be performed in an inert gas atmosphere.

In the manufacturing method for a metal plate according to the present invention, the preparation step may include a rolling step of rolling a base metal made of an iron alloy containing nickel.

In the manufacturing method for a metal plate according to the present invention, the preparation step may include a foil creating step of creating a plating film by using a plating liquid including a solution containing a nickel compound and a solution containing an iron compound.

In the manufacturing method for a metal plate according to the present invention, a thickness of the metal plate may be 85 μm or less.

In the manufacturing method for a metal plate according to the present invention, the metal plate may be for manufacturing the deposition mask by exposing and developing a dry film attached to the first surface of the metal plate to form a first resist pattern, and by etching an area of the first surface of the metal plate, the area being not covered with the first resist pattern.

The present invention is a metal plate used for manufacturing a deposition mask having a plurality of through-holes formed therein, wherein: when a composition analysis of a first surface of the metal plate is performed by using an X-ray photoelectron spectroscopy, a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide; and in the composition analysis of the first surface of the metal plate by means of the X-ray photoelectron spectroscopy, an incident angle of an X-ray emitted to the metal plate on the first surface is 45 degrees, and an acceptance angle of photoelectrons discharged from the metal plate is 90 degrees.

In the metal plate according to the present invention, a thickness of the metal plate may be 85 μm or less.

In the metal plate according to the present invention, the metal plate may be for manufacturing the deposition mask by exposing and developing a dry film attached to the first surface of the metal plate to form a first resist pattern, and by etching an area of the first surface of the metal plate, the area being not covered with the first resist pattern.

The present invention is a manufacturing method for a deposition mask having a plurality of through-holes formed therein, the method comprising: a step of preparing a metal plate; a first resist pattern forming step of forming a first resist pattern on a first surface of the metal plate; and an etching step of etching an area of the first surface of the meal plate, the area being not covered with the resist pattern, so that first recesses to define the through-holes are formed in the first surface of the metal plate; wherein: when a composition analysis of a first surface of the metal plate is performed by using an X-ray photoelectron spectroscopy, a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide; and in the composition analysis of the first surface of the metal plate by means of the X-ray photoelectron spectroscopy, an incident angle of an X-ray emitted to the metal plate on the first surface is 45 degrees, and an acceptance angle of photoelectrons discharged from the metal plate is 90 degrees.

In the manufacturing method for a deposition mask according to the present invention, a thickness of the metal plate may be 85 μm or less.

In the manufacturing method for a deposition mask according to the present invention, the first resist pattern forming step may include a step of attaching a dry film to the first surface of the metal plate, and a step of exposing and developing the dry film to form the first resist pattern.

The present invention is a deposition mask comprising: a metal plate including a first surface and a second surface located oppositely to the first surface; and a plurality of through-holes formed in the metal plate so as to pass through from the first surface of the metal plate to the second surface thereof; wherein: the each through-hole has a second recess formed in the second surface of the metal plate and a first recess formed in the first surface of the metal plate so as to connect to the second recess; when a composition analysis of the first surface the metal plate is performed by using the X-ray photoelectron spectroscopy, a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide; and in the composition analysis of the first surface of the metal plate by means of the X-ray photoelectron spectroscopy, an incident angle of an X-ray emitted to the metal plate on the first surface is 45 degrees, and an acceptance angle of photoelectrons discharged from the metal plate is 90 degrees.

In the deposition mask according to the present invention, a thickness of the metal plate may be 85 μm or less.

According to the present invention, a resist pattern of a narrow width can be stably provided on a surface of a metal plate. Thus, a deposition mask for producing an organic EL display device having a high pixel density can be stably obtained.

DESCRIPTION OF THE PREFERRED EMBODIMENTS

Figure 1:
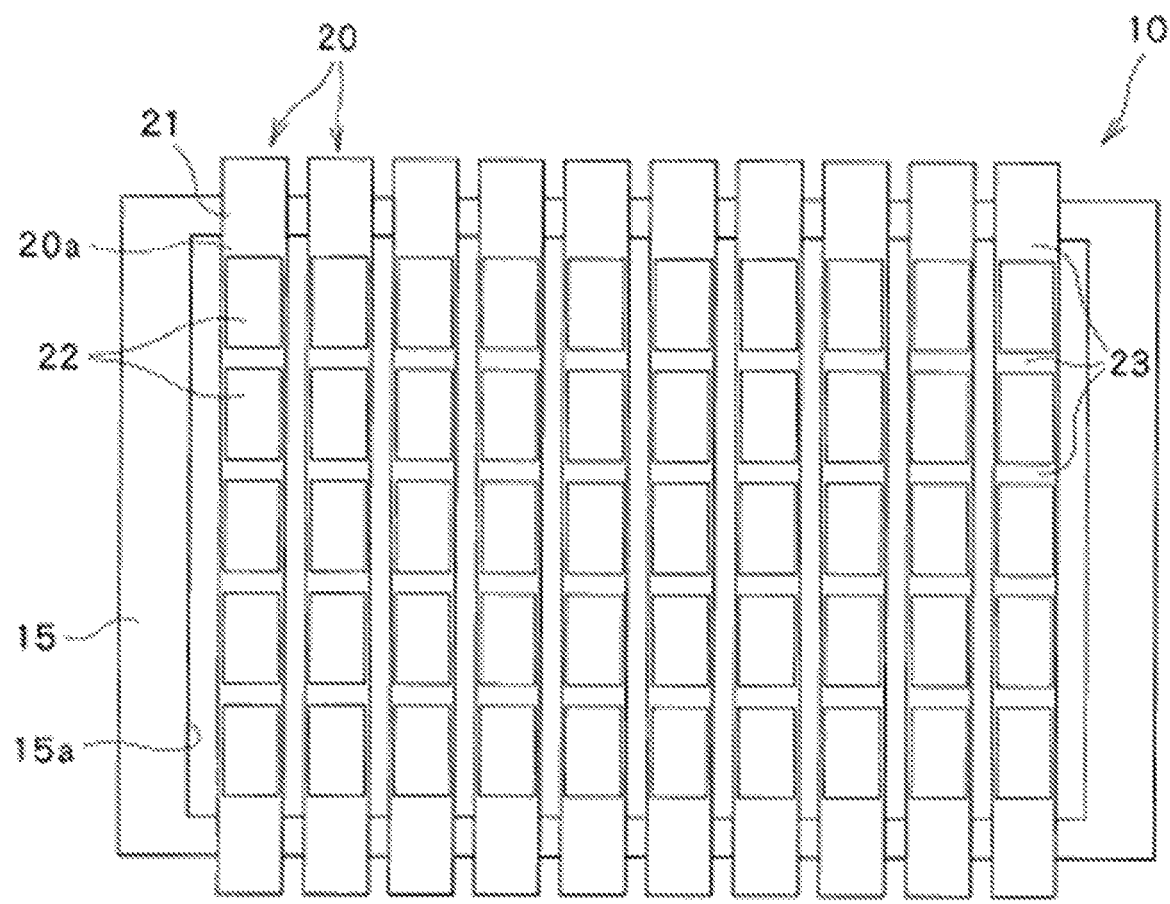
FIG. 1 is a view for explaining an embodiment of the present invention, which is a schematic plan view showing an example of a deposition mask apparatus including a deposition mask.

An embodiment of the present invention will be described herebelow with reference to the drawings. In the drawings attached to the specification, a scale dimension, an aspect ratio and so on are changed and exaggerated from the actual ones, for the convenience of easiness in illustration and understanding.

FIGS. 1 to 20 are views for explaining an embodiment of the present invention and its modification example. In the below embodiment and the modification example, a manufacturing method for a deposition mask for used in patterning an organic material in a desired pattern on a substrate, when an organic EL display apparatus is manufacture, for example. However, not limited thereto, the present invention can be applied to a manufacturing method for a deposition mask for various uses.

In this specification, the terms "plate", "sheet" and "film" are not differentiated from one another based only on the difference of terms. For example, the "plate" is a concept including a member that can be referred to as sheet or film. Thus, for example, "metal plate" is not differentiated from a member that is referred to as "metal sheet" or "metal film" based only on the difference of terms.

In addition, the term "plate plane (sheet plane, film plane)" means a plane corresponding to a plane direction of a plate-like (sheet-like, film-like) member as a target, when the plate-like (sheet-like, film-like) member as a target is seen as a whole in general. A normal direction used to the plate-like (sheet-like, film-like) member means a normal direction with respect to a plate plane (sheet surface, film surface) of the member.

Further, in this specification, terms specifying shapes, geometric conditions and their degrees, e.g., "parallel", "perpendicular", "same", "similar" etc., are not limited to their strict definitions, but construed to include a range capable of exerting a similar function.

(Deposition Mask Apparatus)

Figure 2:
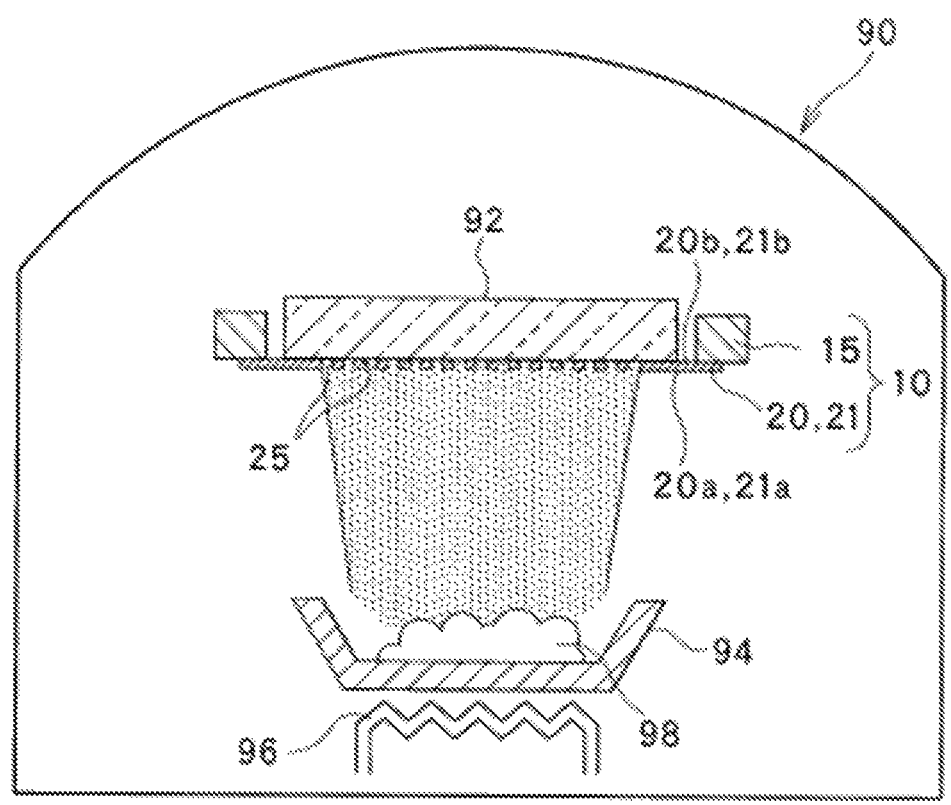
FIG. 2 is a view for explaining a deposition method by using the deposition mask apparatus shown in FIG. 1.
Figure 3:
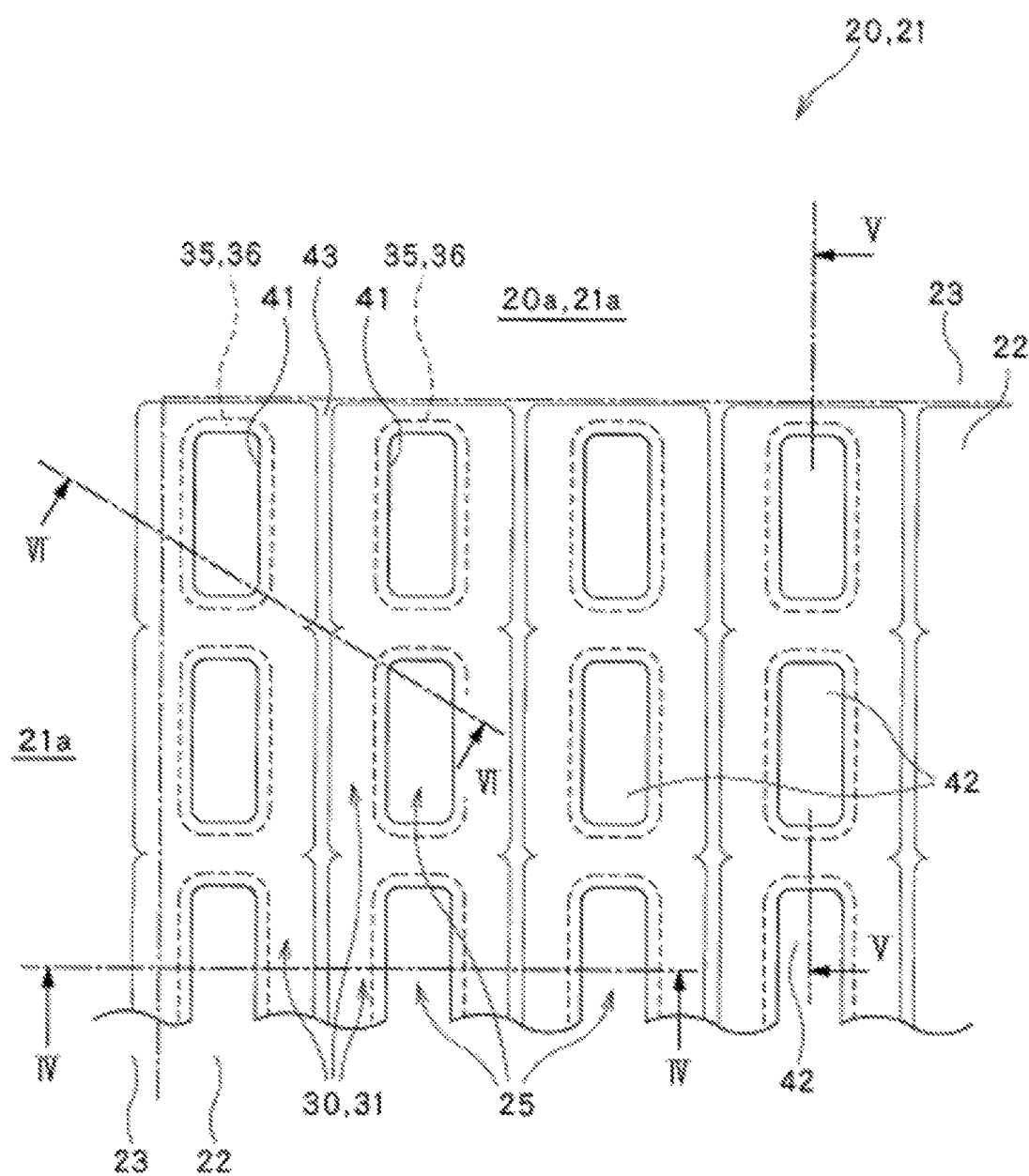
FIG. 3 is a partial plan view showing the deposition mask shown in FIG. 1.
Figure 4:
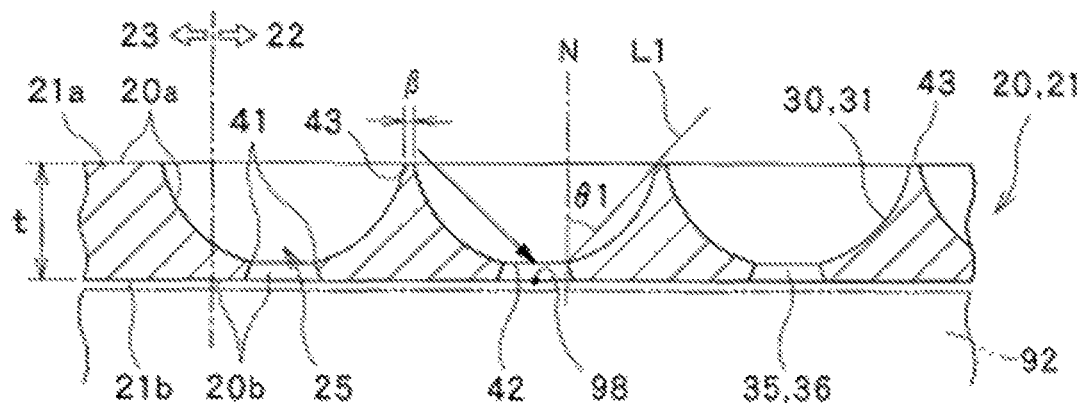
FIG. 4 is a sectional view along the IV-IV line of FIG. 3.
Figure 5:
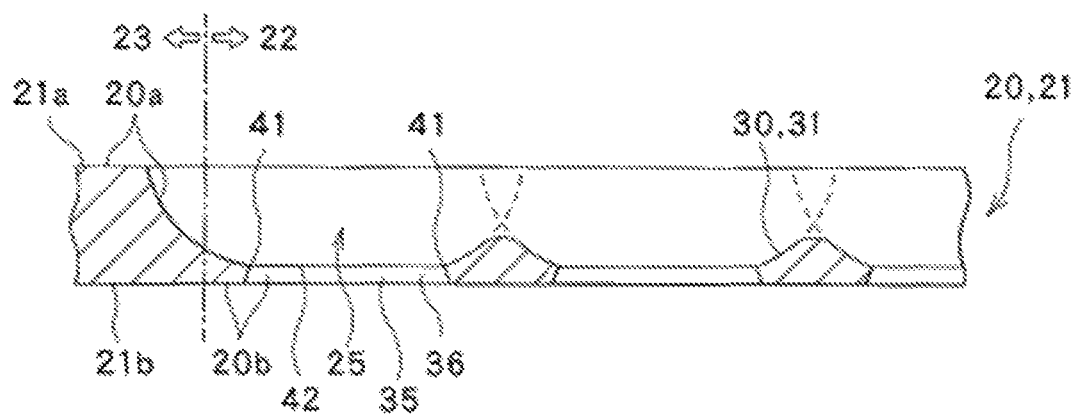
FIG. 5 is a sectional view along the V-V line of FIG. 3.
Figure 6:
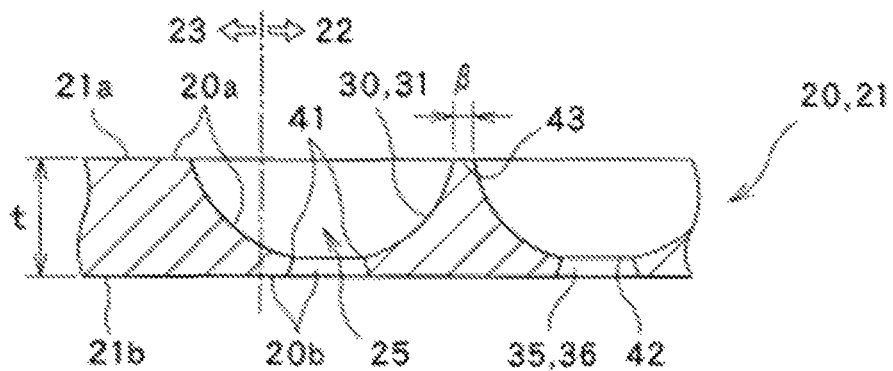
FIG. 6 is a sectional view showing VI-VI line of FIG. 3.

Firstly, an example of a deposition mask apparatus including deposition masks to be manufactured is described with reference mainly to FIGS. 1 to 6. FIG. 1 a plan view showing an example of the deposition mask apparatus including the deposition masks. FIG. 2 is a view for explaining a method for using the deposition mask apparatus shown in FIG. 1. FIG. 3 is a plan view showing the deposition mask seen from a first surface side. FIGS. 4 to 6 are sectional views seen from respective positions of FIG. 3.

The deposition mask apparatus 10 shown in FIGS. 1 and 2 includes a plurality of deposition masks 20 each of which is formed of a metal plate 21 of substantially a rectangular shape, and a frame 15 attached to peripheries of the deposition masks 20. Each deposition mask 20 has a number of through-holes 25 which are formed by etching the metal plate 21, which has a first surface 21a and a second surface 21b located oppositely to the first surface 21a, from both sides of the first surface 21a and the second surface 21b. As shown in FIG. 2, the deposition mask apparatus 10 is used for depositing a deposition material to a substrate. The deposition mask apparatus 10 is supported in a deposition apparatus 90 such that the deposition mask 20 faces a lower surface of the substrate 92 such as a glass substrate, onto which the deposition material is to be deposited.

In the deposition apparatus 90, the deposition mask 20 and the glass substrate 92 are brought into tight contact with each other by a magnetic force of magnets, not shown. In the deposition apparatus 90, there are disposed below the deposition mask apparatus 10 a crucible 94 storing a deposition material (e.g., organic luminescent material) 98 and a heater 96 for heating the crucible 94. The deposition material 98 in the crucible 94 is evaporated or sublimated by heat applied from the heater 96 so as to adhere to the surface of the substrate 92. As described above, since the deposition mask 20 has a lot of through-holes 25 formed therein, the deposition material 98 adheres to the glass substrate 92 through the through-holes 25. As a result, a film of the deposition material 98 is formed on the surface of the substrate 92 in a desired pattern corresponding to the positions of the through-holes 25 of the deposition mask 20.

As described above, in this embodiment, the through-holes 25 are arranged in each effective area 22 in a predetermined pattern. When a color display is desired, an organic luminescent material for red color, an organic luminescent material for green color and an organic luminescent material for blue color may be sequentially deposited, while the deposition mask 20 (deposition mask apparatus 10) and the glass substrate 92 are relatively moved little by little along the arrangement direction of the through-holes 25 (aforementioned one direction). Alternatively, the deposition material 98 may be deposited on the surface of the substrate 92, with the use of the deposition masks 20 that differ depending on colors of the organic luminescent materials.

The frame 15 of the deposition mask apparatus 10 is attached to the peripheries of the rectangular deposition masks 20. The frame 15 is configured to hold each deposition mask in a taut state in order to prevent the deposition mask 20 from warping. The deposition masks 20 and the frame 15 are fixed with respect to each other by spot welding, for example.

The deposition process is performed inside the deposition apparatus 90 in a high-temperature atmosphere. Thus, during the deposition process, the deposition masks 20, the frame 15 and the substrate 92, which are held inside the deposition apparatus 90, are also heated. At this time, each of deposition mask 20, the frame 15 and the substrate 92 develop dimensional change behaviors based on their respective thermal expansion coefficients. In this case, when the thermal expansion coefficients of the deposition mask 20, the frame 15 and the substrate 92 largely differ from one another, positioning displacement occurs because of the difference in dimensional change. As a result, the dimensional precision and the positional precision of the deposition material to be adhered to the substrate 92 lower. In order to avoid this problem, the thermal expansion coefficients of the deposition mask 20 and the frame 15 are preferably equivalent to the thermal expansion coefficient of the substrate 92. For example, when a glass substrate is used as the substrate 92, an iron alloy containing can be used as a main material of the deposition mask 20 and the frame 15. For example, an iron alloy containing 30 to 54% by mass of nickel can be used as a material of the metal plate constituting the deposition masks 20. Concrete examples of an iron alloy containing nickel may be an invar material containing 34-38% by mass of nickel, a super invar material containing cobalt in addition to nickel, or a low thermal expansion Fe—Ni based plated alloy containing 38 to 54% by mass of nickel. In this specification, a numerical range expressed by the symbol "-" includes numerical values sandwiching the symbol "-". For example, a numerical range defined by the expression "34-38% by mass" is identical to a numerical range defined by an expression "not less than 34% by mass and not more than 38% by mass".

(Deposition Mask)

Next, the deposition mask 20 is described in detail. As shown in FIG. 1, in this embodiment, each deposition mask 20 is formed of the metal plate 21, and has an outline of a substantially quadrangular shape in plan view, more precisely, a substantially rectangular shape in plan view. The metal plate 21 of the deposition mask 20 includes the effective area 22 in which the through-holes 25 are formed in a regular arrangement, and a peripheral area 23 surrounding the effective area 22. The peripheral area 23 is an area for supporting the effective area 22, and is not an area through which the deposition material intended to be deposited on the substrate passes. For example, in the deposition mask 20 for use in depositing an organic luminescent material for organic EL display device, the effective area 22 is an area in the deposition mask 20, which faces a section on the substrate to which the organic luminescent material is deposited to form pixels, i.e., a section on the substrate which provides a display surface of the manufactured substrate for organic EL display device. However, for various purposes, the peripheral area 23 may have a through-hole and/or a recess. In the example shown in FIG. 1, each effective area 22 has an outline of a substantially quadrangular shape in plan view, more precisely, a substantially rectangular shape in plan view.

In the illustrated example, the effective areas 22 of the deposition mask 20 are aligned, at predetermined intervals therebetween, along one direction in parallel with a longitudinal direction of the deposition mask 20. In the illustrated example, one effective area 22 corresponds to one organic EL display device. Namely, the deposition mask apparatus 10 (deposition masks 20) shown in FIG. 1 enables a multifaceted deposition.

As shown in FIG. 3, in the illustrate example, a plurality of the through-holes 25 formed in each effective area 22 are arranged at predetermined pitches along two directions perpendicular to each other. An example of the through-hole 25 formed in the metal plate 21 is described in more detail with reference mainly to FIGS. 3 to 6.

As shown in FIGS. 4 to 6, a plurality of the through-holes 25 pass through from the first surface 20a, which is one side along a normal direction of the deposition mask 20, to the second surface 20b, which is the other side among the normal direction of the deposition mask 20. In the illustrated example, as described in more detail below, first recesses 30 are formed in the first surface 21a of the metal plate 21, which serves as the one side in the normal direction of the deposition mask, by an etching process, and second recesses 35 are formed in the second surface 21b, which serves as the other side in the normal direction of the metal plate 21. Each of the first recesses 30 is connected to each of the second recesses 35, so that the second recess 35 and the first recess 30 are formed to communicate with each other. Each through-hole 25 is composed of the second recess 35 and the first recess 30 connected to the second recess 35.

As shown in FIGS. 3 to 6, a cross-sectional area of each first recess 30, in a cross section along a plate plane of the deposition mask 20 at each position along the normal direction of the deposition mask 20, gradually decreases from the side of the first surface 20a of the deposition mask 20 toward the side of the second surface 20b. Similarly, a cross-sectional area of each second recess 35, in a cross section along the plate plane of the deposition mask 20 at each position along the normal direction of the deposition mask 20, gradually decreases from the side of the second surface 20b of the deposition mask 20 toward the side of the first surface 20a.

As shown in FIGS. 4 to 6, a wall surface 31 of the first recess 30 and a wall surface 36 of the second recess 35 are connected via a circumferential connection portion 41. The connection portion 41 is defined by a ridge line of a bulging part where the wall surface 31 of the first recess 30, which inclined with respect to the normal direction of the deposition mask 20, and the wall surface 36 of the second recess 35, which is inclined with respect to the normal direction of the deposition mask 20, are merged with each other. The connection portion 41 defines a through-portion 42 where an area of the through-hole 25 is minimum in plan view of the deposition mask 20.

As shown in FIGS. 4 to 6, the adjacent two through-holes 25 in the other side surface along the normal direction of the deposition mask, i.e., in the second surface 20b of the deposition mask 20, are spaced from each other along the plate plane of the deposition mask. Namely, as in the below-described manufacturing method, when the second recesses 35 are made by etching the metal plate 21 from the side of the second surface 21b of the metal plate 21, which will correspond to the second surface 20b of the deposition mask 20, the second surface 21b of the metal plate 21 remains between the two adjacent second recesses 35.

Similarly, as shown in FIGS. 4 and 6, the two adjacent first recesses 30 may be spaced from each other along the plane of the deposition mask, on the one side along the normal direction of the deposition mask, i.e., on the side of the first surface 20a of the deposition mask 20. Namely, the first surface 21a of the metal plate 21 may remain between the two adjacent first recesses 30. In the below description, a portion of the effective area 22 of the first surface 21a of the meal plate 21, which is not etched and thus remains, is also referred to as top portion 43. By producing the deposition mask 20 such that such a top portion 43 remains, the deposition mask 20 can have a sufficient strength. Thus, it can be prevented that the deposition mask 20 is damaged during transportation, for example. However, when a width β of the top portion 43 is too large, there is a possibility that shadow occurs in the deposition step, which lowers utilization efficiency of the deposition material 98. Thus, the deposition mask 20 is preferably produced such that the width β of the top portion 43 is excessively large. For example, the width β of the top portion 43 is preferably 2 μm or less. In general, the width β of the top portion 43 varies depending on a direction along which the deposition mask 20 is severed. For example, the width β of the top portion 43 shown in FIG. 4 and that of FIG. 6 may differ from each other. In this case, the deposition mask 30 may be formed such that the width β of the top portion 43 is 2 μm or less, regardless of a direction along which the deposition mask 20 is severed.

As shown in FIG. 5, the etching process may be performed such that two adjacent first recesses 30 are connected to each other, depending on their positions. Namely, there may be a part where no first surface 21a of the metal plate 21 remains between two adjacent first recesses 30.

As shown in FIG. 2, the deposition mask apparatus 10 is received in the deposition apparatus 90. In this case, as shown by the two-dot chain lines in FIG. 4, the first surface 20a of the deposition mask 20 is located on the side of the crucible 94 holding the deposition material 98, and the second surface 20b of the deposition mask 20 faces the substrate 92. Thus, the deposition material 98 adheres to the substrate 92 through the first recess 30 whose cross-sectional area gradually decreases. As shown by the arrow in FIG. 4 extending from the first surface 20a toward the second surface 20b, the deposition material 98 not only moves from the crucible 94 toward the substrate 92 along the normal direction of the substrate 92, but also sometimes moves along a direction largely inclined with respect to the normal direction of the substrate 92. At this time, when the thickness of the deposition mask 20 is large, most of the diagonally moving deposition material 98 reaches the wall surface 31 of the first recess 30 to adhere thereto, before the deposition material 98 passes through the through-holes 25 to reach the substrate 92. Thus, in order to improve a utilization efficiency of the deposition material 98, it is considered to be preferable that the thickness t of the deposition mask 20 is reduced so that heights of the wall surface 31 of the first recess 30 and the wall surface 36 of the second recess 35 are reduced. Namely, it can be said that it is preferable that a metal plate 21, which has the thickness t as small as possible as long as the strength of the deposition mask 20 is ensured, is used as the metal plate 21 for constituting the deposition mask 20. In consideration of this point, the thickness t of the deposition mask 20 in this embodiment is preferably set to be 85 μm or less, e.g., within a range of from 5 to 85 μm. The thickness t is a thickness of the peripheral area 23, i.e., a thickness of a part of the deposition mask 20 where the first recess 30 and the second recess 35 are not formed. Therefore, the thickness t can be said as a thickness of the metal plate 21.

In FIG. 4, a minimum angle defined by a line L1, which passes the connection portion 41 having the minimum cross-sectional area of the through-hole 25 and another given position of the wall surface 31 of the first recess 30, with respect to the normal direction N of the deposition mask 20 is represented by a symbol θ1. In order that the diagonally moving deposition material 98 can be caused to reach the substrate 92 without being caused to reach the wall surface 31 as much as possible, it is advantageous that the angle θ1 is increased. In order to increase the angle θ1, it is effective to reduce the aforementioned width β of the top portion 43, as well as to reduce the thickness t of the deposition mask 20.

In FIG. 6, the symbol α represents a width of a portion (hereinafter also referred to as "rib portion") of the effective area 22 of the second surface 21b of the metal plate 21, which it not etched and thus remains. A width α of the rib portion and a size $r_2$ of the through-portion 42 are suitably determined depending on a size of an organic EL display device and its display pixels. Table 1 shows examples of display pixels, a width α of the rib portion and a size $r_2$ of the through-portion which are required depending on the display pixels, in an organic EL display device of 5 inches.

TABLE 1

| Display Pixels | Width of Rib Portion | Size of Through-portion |
| --- | --- | --- |
| FHD (Full High Definition) | 20 μm | 40 μm |
| WQHD (Wide Quad High Definition) | 15 μm | 30 μm |
| UHD (Ultra High Definition) | 10 μm | 20 μm |

Figure 7:
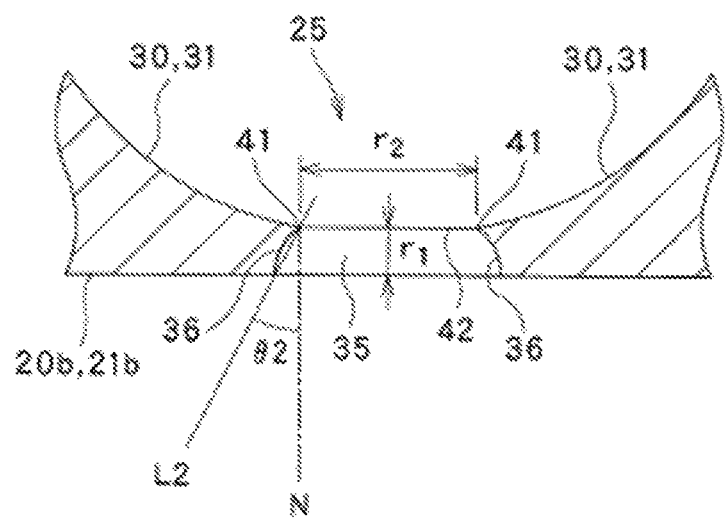
FIG. 7 is an enlarged sectional view showing the through-hole shown in FIG. 4 and an area near thereto.

Although not limited, the deposition mask 20 according to this embodiment is particularly effective when an organic EL display device having a pixel density of 450 ppi or more is produced. Herebelow, a size example of the deposition mask 20 required for producing an organic EL display device having such a high pixel density is described. FIG. 7 is an enlarged sectional view showing the through-hole 25 of the deposition mask 20 shown in FIG. 4 and an area near thereto.

In FIG. 7, as parameters related to the shape of the through-hole 25, a distance from the second surface 20b of the deposition mask 20 up to the connection portion 41 thereof along the normal direction of the deposition mask 20, i.e., a height of the wall surface 36 of the second recess 35 is represented by a symbol $r_1$. Further, a size of the second recess 35 in a part where the second recess 35 is connected to the first recess 30, i.e., a size of the through-portion 42 is represented by a symbol $r_2$. In addition, in FIG. 7, an angle that is defined by a line L2, which connects the connection portion 41 and a distal edge of the second recess 35 in the second surface 21b of the metal plate 21, with respect to the normal line N of the metal plate 21 is represented by a symbol θ2.

When an organic EL display device having a pixel density of 450 ppi or more is produced, the size $r_2$ of the through-portion 42 is preferably set within a range of from 10 to 60 μm. Due to this size, it is possible to provide the deposition mask capable of producing an organic EL display device having a high pixel density. Preferably, the height $r_1$ of the wall surface 36 of the second recess 35 is set 6 μm or less.

Next, the aforementioned angle θ2 shown in FIG. 7 is described. The angle θ2 corresponds to a maximum value of an inclined angle of the deposition material 98 that can reach the substrate 92, out of the deposition material 98 that comes in an inclined manner with respect to the normal direction N of the metal plate 21 and passes through the through-portion 42 near the connection portion 41. This is because the deposition material 98 coming at an inclined angle greater than the angle θ2 adheres to the wall surface 36 of the second recess 35, before the deposition material 98 reaches the substrate 92. Thus, by decreasing the angle θ2, it can be prevented that the deposition material 98 coming at a large inclined angle and passing through the through-portion 42 adheres to the substrate 92. Therefore, it can be prevented that the deposition material 98 adheres to a portion of the substrate 92, which is outside a part overlapping with the through-portion 42. Namely, to decrease the angle θ2 can prevent variation in planar dimension and thickness of the deposition material 98 adhering to the substrate 92. From this point of view, the through-hole 25 is formed such that the angle θ2 is 45 degrees or less. FIG. 7 shows the example in which the size of the second recess 35 in the second surface 21b, i.e., an opening size of the through-hole 25 in the second surface 21b is larger than the size $r_2$ of the second recess 35 in the connection portion 41. Namely, the value of the angle θ2 is a positive value. However, although not shown, the size $r_2$ of the second recess 35 at the connection portion 41 may be larger than the size of the second recess 35 in the connection portion 41. Namely, the value of the angle θ2 may be a negative value.

Next, problems that may occur when the deposition mask 20 is produced are described. Firstly, a manufacturing method for the deposition mask 20 is schematically described with reference to FIGS. 8(a) to 8(c).

Figure 8A:
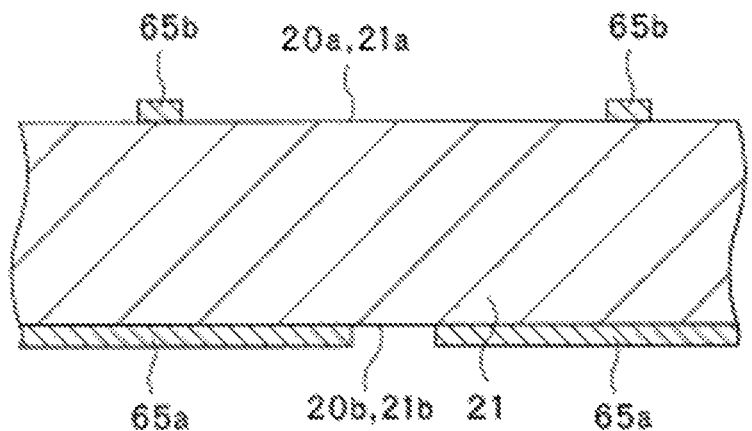
FIGS. 8(a) to 8(c) are views schematically showing a manufacturing method for a deposition mask.
Figure 8B:
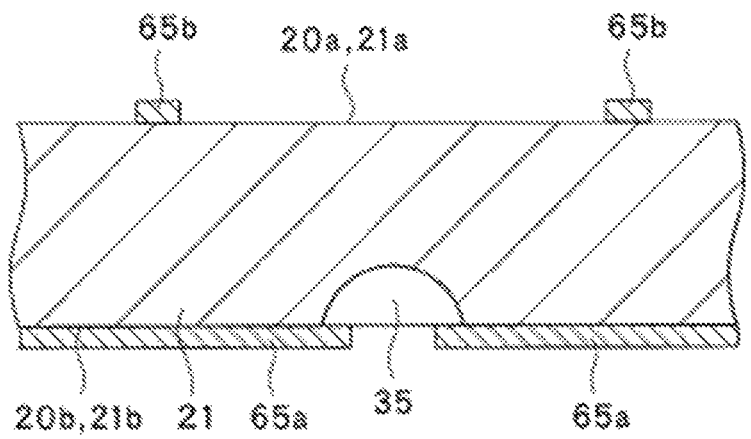
Figure 8C:
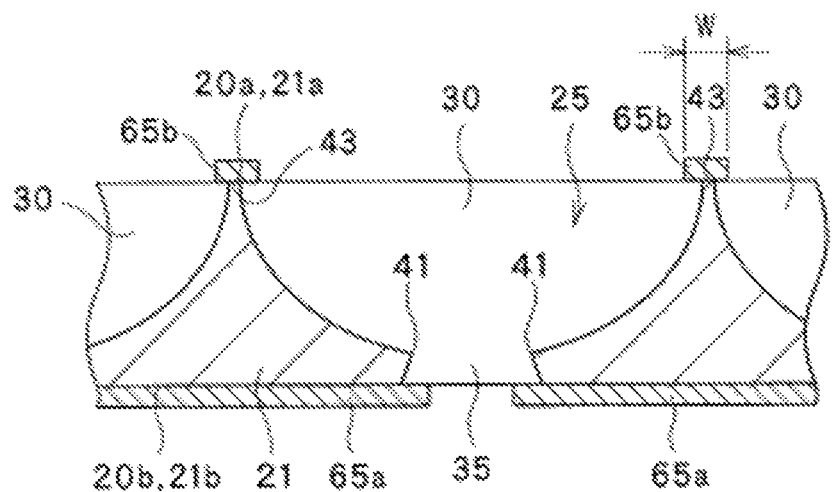

In the manufacturing steps of the deposition mask 20, as shown in FIG. 8(a), a metal plate 21 having a first surface 21a and a second surface 21b is firstly prepared. In addition, as shown in FIG. 8(a), a first resist pattern 65a is formed on the first surface 21a of the metal plate 21, and a second resist pattern 65b is formed on the second surface 21b. Thereafter, as shown in FIG. 8(b), a second surface etching step of forming a second recess 35 is performed by etching an area of the second surface 21b of the metal plate 21, which is not covered with the second resist pattern 65b. Then, as shown in FIG. 8(c), a first etching step of forming a first surface recess 30 is performed by etching an area of the first surface 21a of the metal plate 21, which is not covered with the first resist pattern 65a.

As described above, in order to increase the utilization efficiency of the deposition material 98 while the deposition mask 20 has a sufficient strength, it is preferable that the top portion 43 having a width as small as possible remains. In this case, in accordance with such a top portion 43, a width w of the first resist pattern 65a formed on the first surface 21a of the metal plate 21 becomes also smaller. As shown in FIGS. 8(a) and 8(b), erosion in the metal plate 21 by the etching steps takes place not only in the normal direction (thickness direction) of the metal plate 21 but also in a direction along the plane of the metal plate 21. Thus, when the width w of the first resist pattern 65a is smaller than the degree of erosion that takes place in the direction along the plate plane of the metal plate 21, the resist pattern 65a peels off from the first surface 21a of the metal plate 21 during the etching step. The erosion that takes place in the direction along the plate plane of the metal plate 21 is considered to be at least about 3 μm on one side. Taking this point into consideration, the width w of the first resist pattern 65a is preferably set to be larger than the width β of the aforementioned top portion 43 by at least 6 μm. For example, the width w of the first resist pattern 65a is within a range of from 20 to 40 μm, for example.

In order to precisely create the first resist pattern 65a of a narrow width, a below-described resist film 65c for forming the resist pattern 65a is required to have a high resolution. For example, a so-called dry film such as a resist film containing acryl-based photo-setting resin is preferably used as the resist film 65c. An example of the dry film may be RY3310 manufactured by Hitachi Chemical Co., Ltd. In addition, other examples of the dry film may be UFG-052 and ATP-053 manufactured by ASAHI KASEI E-materials Corp. and so on.

The dry film means a film that is attached to an object such as the metal plate 21, in order to form a resist film on the object. The dry film includes at least a base film made of, e.g., PET, and a photosensitive layer having photosensitivity, which is laminated on the base film. The photosensitive layer contains a photosensitive material such as acryl-based resin, an epoxy-based resin, a polyimide-based resin, a styrene-based resin and so on.

By producing the first resist pattern 65a by means of a dry film having a high resolution, it is possible to precisely form the first resist pattern 65a having a small width w on the first surface 21a of the metal plate 21. On the other hand, when the width w of the first resist pattern 65 becomes small, a contact planar dimension between the first surface 21a of the metal plate 21 and the first resist pattern 65a becomes also small. Thus, the below-described resist film 65c for forming the first resist pattern 65a is required to have a high adhesion force to the first surface 21a of the metal plate 21.

However, the present inventors have conducted extensive studies and found that, although the dry film strongly adheres to copper and copper alloy, the dry film is difficult to adhere to an iron-nickel alloy such as an invar material. Thus, the conventional manufacturing process of the deposition mask 20 has a trouble in which the first resist pattern 65a and/or the second resist pattern 65b peel/peels off from the metal plate 21. For example, in a developing step of developing the below-described exposed resist film 65c, 65d to form a resist pattern 65a, 65b, it was observed that a developing solution penetrated between the metal plate 21 and the resist film 65c, 65d so that the resist film 65c, 65d peeled off from the metal plate 21. In addition, after the developing step and before a baking step of baking the resist pattern 65a, 65b in order to more securely adhere the resist pattern 65a, 65b to the metal plate 21, it was observed that the resist film 65c, 65d peeled off from the metal plate 21.

As an etching resist, a liquid resist material that is applied to an object while it is in a flowable state, e.g., in a liquid state is widely known, in addition to the aforementioned dry film. The liquid resist material is a casein resist, for example. In this case, a resist film is formed on an object such as the metal plate 21 by applying the liquid resist material onto the object and solidifying the liquid. The liquid resist material comes into contact with the object, while it is in the liquid state. Thus, even when the surface of the object has a concavity and/or convexity, the liquid solidifies to become a resist film after the liquid followed the concavity and/or convexity. Thus, an adhesion property between the liquid resist material and the object is high.

On the other hand, as described above, the dry film comes into contact with the object, while it is in the state of a film containing a photosensitive layer. Thus, when there is concavity and/or convexity on the surface of the object, the photosensitive layer of the dry film cannot completely follow the concavity and/or convexity. As a result, an adhesion property between the dry film and the object is lower than the adhesion property between the liquid resist material and the object.

Table 2 shows a comparison result between the dry film and the liquid resist material as to a resolution, an adhesion property and a cost. The term "adhesion property" herein means easiness of the dry film or the liquid resist material to the invar material. As shown in Table 2, the conventional dry film is poor in adhesion property to the invar material and costly, while it has an excellent resolution as compared with the liquid resist material.

TABLE 2

|  | Resolution | Adhesion Property | Cost |
| --- | --- | --- | --- |
| Dry Film | Great | Not good | Not good |
| Liquid Resist Material | Not good | Good | Great |

The dry film has been conventionally used for producing a copper wiring by etching a copper foil for a print substrate. In this case, the dry film is provided on the copper foil. As described above, since the dry film strongly adheres to copper and copper alloy, a problem related to the adhesion property of the dry film has not specifically drawn attention. It is considered that the problem of poor adhesion property of the dry film to an iron-nickel alloy such as invar material draws attention when a resist pattern of a small width is precisely formed on a metal plate made of an iron-nickel alloy.

In order to stably form the first resist pattern 65a having a small width w on the first surface 21a of the metal plate 21 made of an iron-nickel alloy, it is important to improve the adhesion force between the first resist pattern 65a and the first surface 21a. The present inventors have conducted extensive studies and found that the adhesion force between the first resist pattern 65a and the first surface 21a depends on the presence of a nickel compound in the first surface 21a of the metal plate 21. The fact found by the present inventors is described below.

In general, when a surface of a metal plate made of an iron alloy containing nickel is oxidized, the metal plate includes a bulk layer made of an iron alloy containing nickel, and a surface layer containing iron oxide, iron hydroxide, nickel oxide and nickel hydroxide. To be specific, there are iron oxide and iron hydroxide on a part closest to the surface of the metal plate, and there are nickel oxide and nickel hydroxide between the iron oxide and the iron hydroxide, and the bulk layer.

The present inventors analyzed a composition of the metal plate with its surface being oxidized by using an X-ray photoelectron spectroscopy (also referred to as XPS method herebelow), and observed that a bulk layer made of an iron alloy containing nickel existed at a position within several nanometers from the surface of the metal plate. Namely, it can be said that a surface layer containing nickel oxide and nickel hydroxide exists at a position within several nanometers from the surface of the metal plate.

In addition, as shown in the below-described Examples, the present inventors evaluated an adhesion property of the metal plate to a resist pattern was evaluated, and found that, as compared with a metal plate having a high adhesion property to a resist pattern, a metal plate having a low adhesion property to a resist pattern had more nickel oxide and nickel hydroxide in the surface layer of the metal plate. In consideration that compounds existing in the surface layer of the metal plate are iron oxide, iron hydroxide, nickel oxide and nickel hydroxide, the condition in which "more nickel oxide and nickel hydroxide exist in the surface layer of the metal plate" can be said as a condition in which "a ratio of nickel oxide and nicely hydroxide relative to iron oxide and iron hydroxide is higher in the surface layer of the metal plate". In addition, as shown in the below-described Examples, the present inventors evaluated adhesion properties of various metal plates to a resist pattern, and found that, when a ratio of nickel oxide and nickel hydroxide relative to iron oxide and iron hydroxide was 0.4 or less, the adhesion property of a metal plate to a resist pattern could be sufficiently ensured, and that when the aforementioned ratio exceeded 0.4, the adhesion property of a metal plate to a resist pattern was insufficient.

In addition, as to a metal plate having a high adhesion property to a resist pattern and a metal plate having a low adhesion property to a resist pattern, the present inventors examined difference in manufacturing steps between these metal plates. The present inventors found that the metal plate having a low adhesion property to a resist pattern was subjected to an annealing step of annealing the metal plate under a reduction atmosphere containing a lot of reducing gas such as hydrogen. Thus, it can be said that, under a reduction atmosphere, nickel oxide and nickel hydroxide tend to segregate on the surface of the metal plate. In addition, as shown in the below-described reaction formula, under a reduction atmosphere containing a lot of reducing gas such as hydrogen, nickel hydroxide is generated in accordance with a reduction reaction of nickel oxide. Thus, it is considered that nickel hydroxide has a larger negative impact on the adhesion property to a resist pattern than nickel oxide does.

Based on the above examination, it can be said that an adhesion property of a metal plate to a resist pattern can be expected based on a ratio of nickel hydroxide in the surface layer of the metal plate. However, as shown in the below-described Examples, in the XPS analysis, it is not easy to accurately separate a peak corresponding to nickel oxide and a peak corresponding to nickel hydroxide. In consideration thereof, this embodiment employs a method for obtaining information about the adhesion property to a resist pattern, based on a ratio of nickel oxide and nickel hydroxide relative to iron oxide and iron hydroxide. A concrete existence ratio and details of a method for inspecting respective compounds in the first surface 21a of the metal plate 21 will be described later.

Next, an operation and an effect of this embodiment as structured above are described.

Herein, a manufacturing method for a metal plate used for manufacturing a deposition mask is firstly described. Then, a method for manufacturing a deposition mask using the obtained metal plate is described.

After that, a method for depositing a deposition material on a substrate using the obtained deposition mask is described.

(Manufacturing Method for Metal Plate)

Figure 9A:
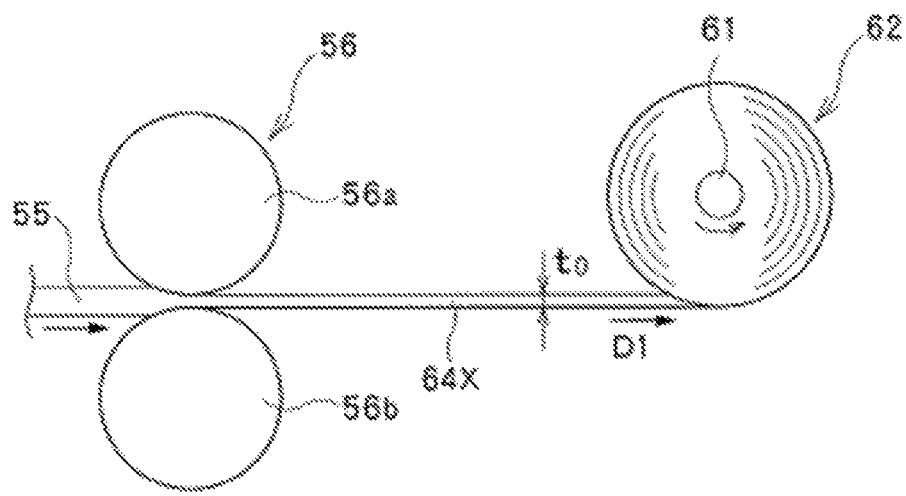
FIG. 9(a) is a view showing a step of obtaining a metal plate having a desired thickness by roll a base metal.
Figure 9B:
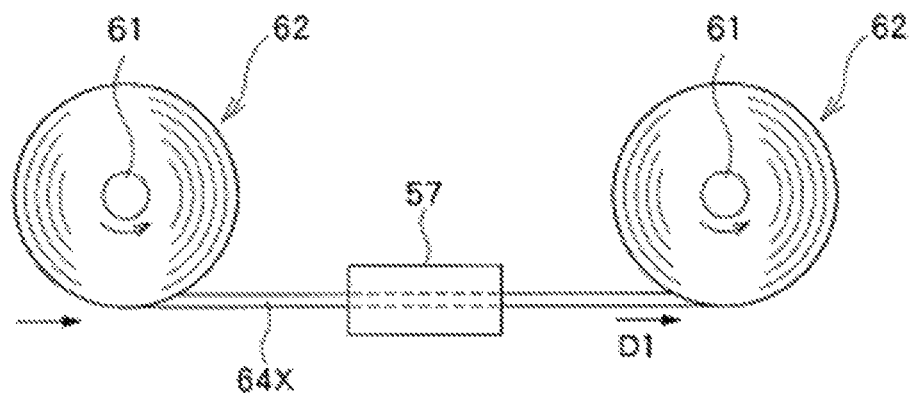
FIG. 9(b) is a view showing a step of annealing the metal plate obtained by rolling.

A method for manufacturing a metal plate is firstly described with reference to FIGS. 9(a) and 9(b). FIG. 9(a) is a view showing a step of rolling a base metal to obtain a metal plate having a desired thickness. FIG. 9(b) is a view showing a step of annealing the metal plate obtained by the rolling step.

<Rolling Step>

As shown in FIG. 9(a), a base metal 55 made of an iron alloy containing nickel is prepared, and the base metal 55 is transported toward a rolling apparatus 56 including a pair of reduction rolls 56a and 56b along a transport direction shown by the arrow D1. The base metal 55 having reached between the pair of reduction rolls 56a and 56b is rolled by the pair of reduction rolls 56a and 56b. Thus, a thickness of the base metal 55 is reduced and is elongated along the transport direction. As a result, a plate member 64X having a thickness $t_0$ can be obtained. As shown in FIG. 9(a), a winding body 62 may be formed by winding up the plate member 64X around a core 61. A concrete value of the thickness $t_0$ is within a range of from 5 to 85 μm, as described above.

FIG. 9(a) merely shows the rolling step schematically, and a concrete structure and procedure for performing the rolling step are not specifically limited. For example, the rolling step may include a hot rolling step of processing the base metal at a temperature not less than a recrystallization temperature of the invar material constituting the base metal 55, and a cold rolling step of processing the base metal at a temperature not more than the recrystallization temperature of the invar material. In addition, an orientation along which the base metal 55 and the plate member 64X pass through between the reduction rolls 56a and 56b is not limited to one direction. For example, in FIGS. 9(a) and 9(b), the base metal 55 and the plate member 64X may be gradually rolled by repeatedly passing the base metal 55 and the plate member 64X through between the pair of reduction rolls 56a and 56b in an orientation from the left side to the right side in a sheet plane, and in an orientation from the right side to the left side in the sheet plane.

<Slitting Step>

After that, there may be performed a slitting step of slitting both ends of the plate member 64X, which is obtained by the rolling step, in the width direction thereof, over a range of from 3 to 5 mm. The slitting step is performed to remove a crack that may be generated on both ends of the plate member 64X because of the rolling step. Due to the slitting step, it can be prevented that a breakage phenomenon of the plate member 64X, which is so-called plate incision, occurs from the crack as a starting point.

<Annealing Step>

After that, in order to remove a remaining stress accumulated by the rolling process in the plate member 64X, as shown in FIG. 9(b), the plate member 64X is annealed by using an annealing apparatus 57, so that an elongated metal plate 64 is obtained. As shown in FIG. 9(b), the annealing step may be performed while the plate member 64X or the elongated metal plate 64 is being pulled in the transport direction (longitudinal direction). Namely, the annealing step may be performed as a continuous annealing process while the elongated metal plate is being transported, instead of a batch-type annealing process. A duration of the annealing step is suitably set depending on a thickness of the elongated metal plate 64 and a reduction ratio thereof. For example, the annealing step is performed for 60 seconds or more at 500° C. The above "60 seconds" mean that it takes 60 seconds for the plate member 64X to pass through a space, which is heated at a temperature of 500° C. in the annealing apparatus 57.

The aforementioned annealing step is preferably performed in an irreducible atmosphere or an inert gas atmosphere. The irreducible atmosphere herein means an atmosphere free of reducing gas such as hydrogen. The expression "free of reducing gas" means that a concentration of reducing gas such as hydrogen is 10% or less. In addition, the inert gas atmosphere means an atmosphere where inert gas such as argon gas, helium gas, or nitrogen gas exists 90% or more. By performing the annealing step in the irreducible atmosphere or the inert gas atmosphere, it can be prevented that the aforementioned nickel hydroxide is generated on a first surface 64a and a second surface 64b of the elongated metal plate 64.

By performing the annealing step, it is possible to obtain the elongated metal plate 64 of a thickness $t_0$, from which the remaining strain is removed to a certain extent. The thickness $t_0$ is generally equal to a thickness t of the deposition mask 20.

The elongated metal plate 64 having the thickness $t_0$ may be made by repeating the above rolling step, the slitting step and the annealing step a plurality of times. FIG. 9(b) shows the example in which the annealing step is performed while the elongated metal plate 64 is being pulled in the longitudinal direction. However, not limited thereto, the annealing step may be performed to the elongated metal plate 64 that is wound around the core 61. Namely, the batch-type annealing process may be performed. When the annealing step is performed while the elongated metal plate 64 is wound around the core 61, the elongated metal plate 64 may have a warping tendency corresponding to a winding diameter of the winding body 62. Thus, depending on a winding diameter of the winding body 62 and/or a material forming the base metal 55, it is advantageous to perform the annealing step while the elongated metal plate 64 is being pulled in the longitudinal direction.

<Severing Step>

After that, there is performed a severing step of severing both ends of the elongated metal plate 64 in the width direction thereof over a predetermined range, so as to adjust the width of the elongated metal plate 64 into a desired width. In this manner, the elongated metal plate 64 having a desired thickness and a desired width can be obtained.

<Inspection Step>

After that, there is performed an inspection step of inspecting a composition of the material constituting the first surface 64a of the obtained elongated metal plate 64. Herein, there is explained an example in which a composition analysis of the first surface 64a of the elongated metal plate 64 is performed by the XPS method. The XPS method is method in which a specimen is irradiated with an X-ray, and an energy distribution of photoelectrons discharged from the specimen is measured to obtain information about types of constituent elements and/or an existence amount thereof in an area within a range of several nanometers from a surface of the specimen. In this case, in a spectrum measured by the X-ray photoelectron spectroscopy, an existence amount of each constituent element is proportionate to a peak planar dimension value calculated by integrating a peak planar dimension corresponding to each constituent element. Thus, a peak planar dimension value corresponding to each constituent element is firstly calculated, a total value of the peak planar dimension values of the respective constituent elements is then calculated, and thereafter an atomic % of a target constituent element can be calculated by dividing a peak planar dimension value of the target constituent element by the total value and multiplying the value by 100. A relationship between an existence amount of a given constituent element and a peak planar dimension value thereof may differ from one another depending on sensitivity to an X-ray and so on. In this case, the aforementioned total value and the atomic % may be calculated after a peak planar dimension value of each constituent element is multiplied by a relative sensitivity coefficient for compensating the sensitivity difference so as to calculate a compensated peak planar dimension value.

Figure 10:
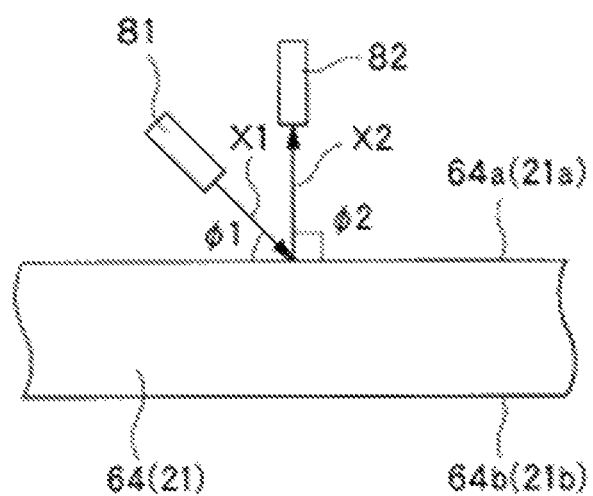
FIG. 10 is a view showing that a composition analysis of a first surface of the metal plate is performed by using an X-ray photoelectron spectroscopy.

FIG. 10 is a view showing that a composition analysis of the first surface 64a of the elongated metal plate 64 is performed by using the X-ray photoelectron spectroscopy. As shown in FIG. 10, in one example of the composition analysis of the first surface 64a of the elongated metal plate 64, an X-ray X1 is emitted from an irradiation unit 81 to the elongated metal plate 64, and an acceptance angle of a photoelectron X2 discharged from the elongated metal plate 64 is set at 90 degrees. In this case, types of constituent elements and their existence amounts in an area within a range of several nanometers, e.g., 5 nm from the first surface 64a of the elongated metal plate 64 can be measured in an improved reproducible fashion. As shown in FIG. 10, the "acceptance angle" is an angle defined by a direction along which the photoelectron X2, which is to be discharged from the elongated metal plate 64 to reach a detection unit 82, travels when the photoelectron X2 is discharged from the elongated metal plate 64, and the first surface 64a of the elongated metal plate 64.

After the composition analysis of the first surface 64a of the elongated metal plate 64 was performed by means of the XPS method, there is performed selection of an elongated metal plate 64 in which only the elongated metal plate 64 that satisfies the following condition (1) is used in a manufacturing step of the deposition mask 20, which is described below.

(1) When the composition analysis of the first surface 64a of the elongated metal plate 64 is performed by using the X-ray photoelectron spectroscopy, a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide.

The aforementioned condition (1) is a condition for sufficiently ensuring an adhesion force between the below-described first resist pattern 65a and the first surface 21a. As described above, nickel hydroxide and nickel oxide function so as to decrease the adhesion force between the first resist pattern 65a and the first surface 21a. Thus, determining upper limits of nickel oxide and a peak planar dimension value of nickel oxide, as determined by the aforementioned condition (1), is effective to ensure a minimum adhesion force required as the adhesion force between the first resist pattern 65a and the first surface 21a.

As described later, in an analysis using the X-ray photoelectron spectroscopy, since a peak corresponding to nickel oxide and a peak corresponding to nickel hydroxide exist extremely close to each other, it is difficult to definitely differentiate these peaks. Similarly, since a peak corresponding to iron oxide and a peak corresponding to iron hydroxide exist extremely close to each other, it is difficult to definitely differentiate these peaks. From this analytic point of view, in this embodiment, whether an adhesion force between the first resist pattern 65a and the first surface 21a can be sufficiently ensured or not is judged based on a ratio between a sum of a peak planar dimension value of nickel oxide and a peak planar dimension value of nickel hydroxide, and a sum of a peak planar dimension value of iron oxide and a peak planar dimension value of iron hydroxide, instead of a ratio between a peak planar dimension value of nickel hydroxide and a peak planar dimension value of iron hydroxide.

The present inventors have conducted extensive studies and found that, when an atmosphere upon annealing step contains reducing gas such as hydrogen, nickel hydroxide is likely to be generated on the first surface 64a and the second surface 64b of the elongated metal plate 64, so that the adhesion force between the first resist pattern 65a and the first surface 21a is likely to decrease. When an atmosphere upon annealing step was an irreducible atmosphere or an inert gas atmosphere, it could be prevented that nickel hydroxide was generated on the first surface 64a and the second surface 64b of the elongated metal plate 64. Thus, since the above A1/A2 was made to be 0.4 or less, an adhesion force between the first resist pattern 65a and the first surface 21a could be sufficiently ensured.

Under a reduction atmosphere containing reducing gas such as hydrogen, as shown by the below reaction formula, it is considered that a part of nickel oxide, which has been already formed on the surface of the elongated metal plate 64, is reduced to generate nickel, and that, simultaneously therewith, nickel hydroxide is generated on the surface of the elongated metal plate 64.

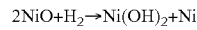

In order to sufficiently ensure the adhesion force between the first resist pattern 65a and the first surface 21a, it is important that generation of a nickel reduction reaction on the surface of the elongated metal plate 64, such as the first surface 64a and the second surface 64b, so as to prevent generation of nickel hydroxide.

The present inventors have conducted extensive studies and found that, as A1/A2 becomes lower, the adhesion property between the first resist pattern 65a and the first surface 21a tends to increase. Thus, in order to improve the adhesion property between the first resist pattern 65a and the first surface 21a, A1/A2 is preferably 0.3 or less, and more preferably A1/A2 is 0.2 or less.

In the above description, the inspection step of inspecting the elongated metal plate 64 based on the aforementioned condition (1) is utilized for selecting the elongated metal plate 64, for example. However, the use of the condition (1) is not limited thereto.

For example, the aforementioned condition (1) may be utilized for optimizing a condition of manufacturing the elongated metal plate 64, such as an annealing temperature, an annealing period of time and so on. To be specific, the condition (1) may be utilized for an operation in which the elongated metal plates 64 are manufactured at various annealing temperatures for various annealing periods of time, compositions of a surface of each obtained elongated metal plate 64 are analyzed, and the analysis result and the condition (1) are compared to each other so as to set a suitable manufacturing condition that satisfies the condition (1). In this case, it is not necessary that the selection based on the condition (1) is performed for all the elongated metal plates 64 obtained in the actual manufacturing steps. For example, a sampling inspection regarding the condition (1) may be performed only for some of the elongated metal plates 64. Alternatively, after a manufacturing condition has been once set, the inspection regarding the condition (1) may not be performed at all.

(Method for Manufacturing Deposition Mask)

Next, a method for manufacturing the deposition mask 20 by using the elongated metal plate 64 selected as described above is described with reference mainly to FIGS. 11 to 19. In the below-described method for manufacturing the deposition mask 20, as shown in FIG. 11, the elongated metal plate 64 is supplied, the through-holes 25 are formed in the elongated metal plate 64, and the elongated metal plate 64 are severed so that the deposition masks 20 each of which is formed of the sheet-like metal plate 21 are obtained.

To be more specific, the method for manufacturing a deposition mask 20 includes a step of supplying an elongated metal plate 64 that extends like a strip, a step of etching the elongated metal strip 64 using the photolithographic technique to form a first recess 30 in the elongated metal plate 64 from the side of a first surface 64a, and a step of etching the elongated metal plate 64 using the photolithographic technique to form a second recess 35 in the elongated metal plate 64 from the side of a second surface 64b. When the first recess 30 and the second recess 35, which are formed in the elongated metal plate 64, communicate with each other, the through-hole 25 is made in the elongated metal plate 64. In the example shown in FIGS. 12 to 19, the step of forming the second recess 35 is performed before the step of forming the first recess 30. In addition, between the step of forming the second recess 35 and the step of forming the first recess 30, there is further provided a step of sealing the thus made second recess 35. Details of the respective steps are described below.

Figure 11:
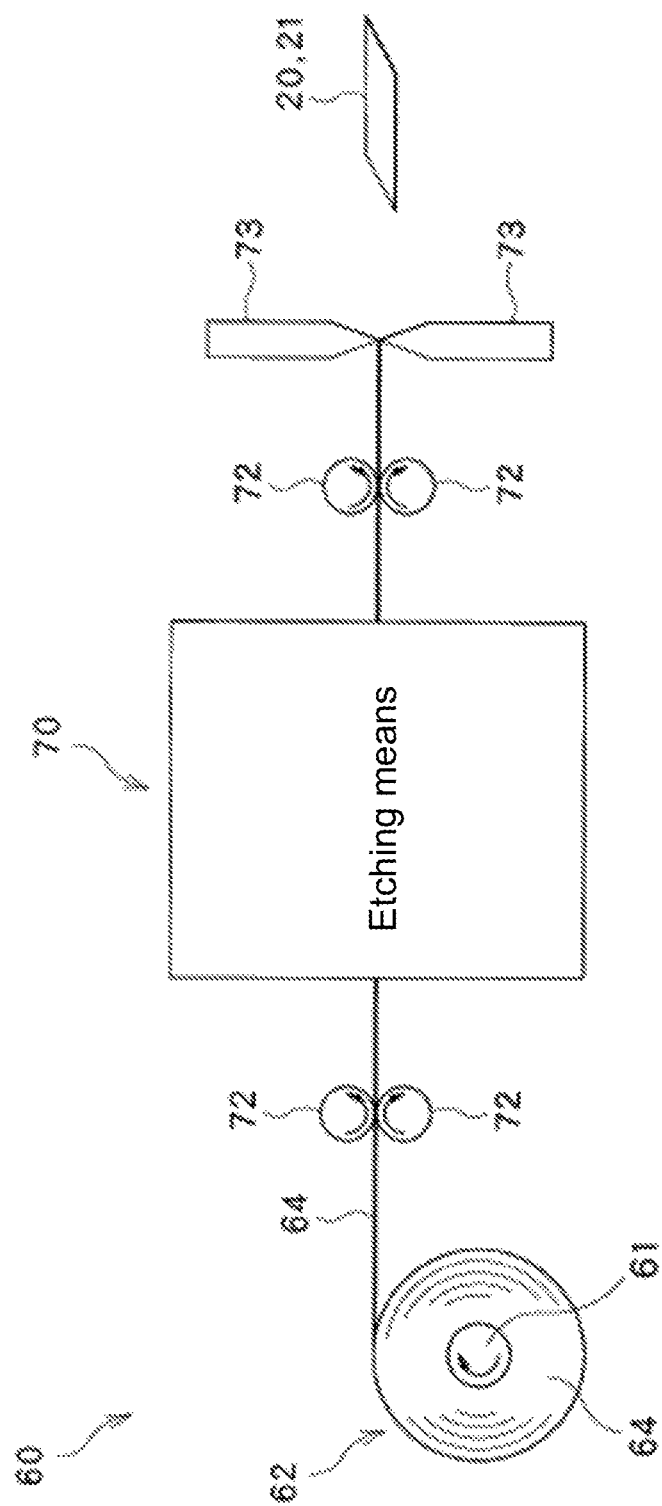
FIG. 11 is a schematic view for generally explaining an example of a manufacturing method for the deposition mask shown in FIG. 1.

FIG. 11 shows a manufacturing apparatus 60 for making the deposition masks 20. As shown in FIG. 11, the winding body 62 having the core 61 around which the elongated metal plate 64 is wound is firstly prepared. By rotating the core 61 to unwind the winding body 62, the elongated metal plate 64 extending like a strip is supplied as shown in FIG. 11. After the through-holes 25 are formed in the elongated metal plate 64, the elongated metal plate 64 provides the sheet-like metal plates 21 and further the deposition masks 20.

The supplied elongated metal plate 64 is transported by the transport rollers 72 to an etching apparatus (etching means) 70. The respective processes shown in FIGS. 12 to 19 are performed by the etching means 70. In this embodiment, a plurality of the deposition masks 20 are assigned in the width direction of the elongated metal plate 64. Namely, the deposition masks 20 are made from an area occupying a predetermined position of the elongated metal plate 64 in the longitudinal direction. In this case, it is preferable that the deposition masks 20 are assigned to the elongated metal plate 64 such that the longitudinal direction of each deposition mask 20 corresponds to the rolling direction D1 of the elongated metal plate 64.

Figure 12:
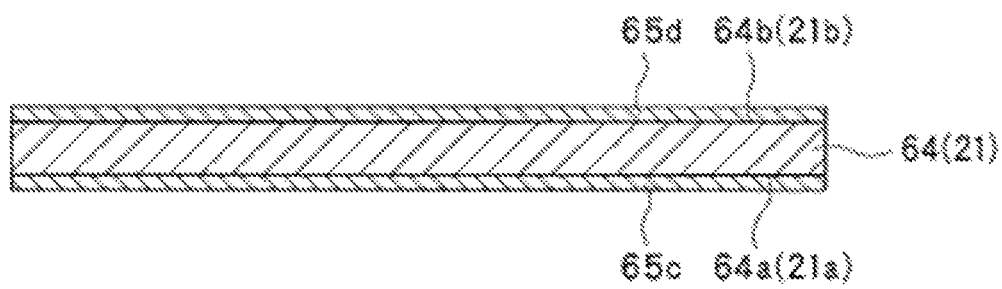
FIG. 12 is a view for explaining an example of the manufacturing method for the deposition mask, which is a sectional view showing a step of forming a resist film on the metal plate.

As shown in FIG. 12, resist films 65c and 65d each containing a negative-type photosensitive resist material are firstly formed on the first surface 64a and the second surface 64b of the elongated metal plate 64. As a method for forming the resist films 65c and 65d, there is employed a method in which a film on which a layer containing a photosensitive resist material, such as an acryl-based photo-setting resin is formed, i.e., a so-called dray film is attached to the first surface 64a and the second surface 64b of the elongated metal plate 64. As described above, the elongated metal plate 64 is manufactured such that an existence amount of nickel hydroxide in the first surface 64a satisfies the aforementioned condition (1). The resist film 65c is attached to such a first surface 64a.

Figure 13:
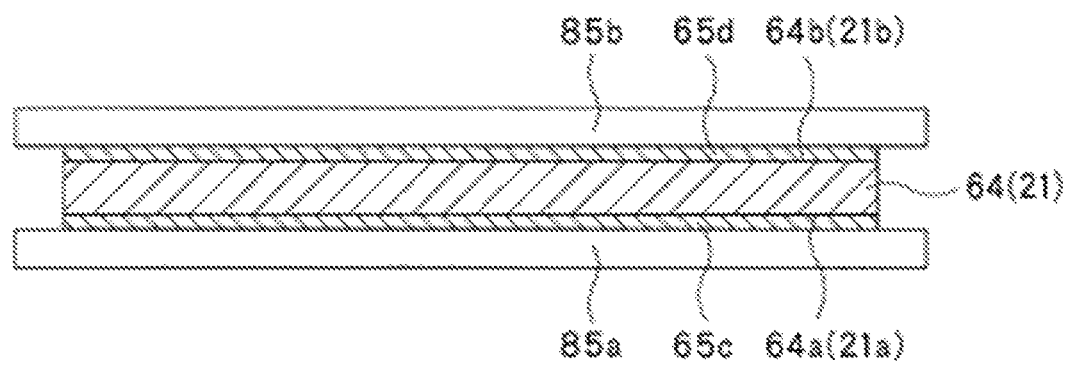
FIG. 13 is a view for explaining an example of the manufacturing method for the deposition mask, which is a sectional view showing a step of bringing an exposure mask into tight contact with the resist film.

Then, exposure masks 85a and 85b which do not allow light to transmit through areas to be removed of the resist films 65c and 65d are prepared. As shown in FIG. 13, the masks 85a and 85b are located on the resist films 65c and 65d. For example, glass dry plates which do not allow light to transmit through the areas to be removed from the resist films 65c and 65d are used as the exposure masks 85a and 85b. Thereafter, the exposure masks 85a and 85b are sufficiently brought into tight contact with the resist films 65c and 65d by vacuum bonding.

A positive-type photosensitive resist material may be used. In this case, there is used an exposure mask which allows light to transmit through an area to be removed of the resist film.

Figure 14A:
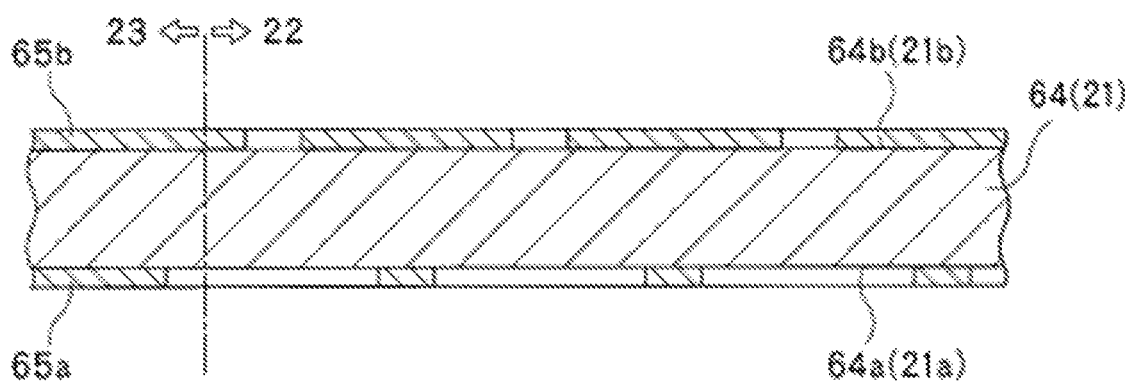
FIG. 14A is a view for explaining an example of the manufacturing method for the deposition mask, showing an elongated metal plate in a section along a normal direction.

After that, the resist films 65c and 65d are exposed through the exposure masks 85a and 85b. Further, the resist films 65c and 65d are developed (developing step) in order to form an image on the exposed resist films 65c and 65d. Thus, as shown in FIG. 14A, a first resist pattern 65a can be formed on the first surface 64a of the elongated metal plate 64, and a second resist pattern 65b can be formed on the second surface 64b of the elongated metal plate 64. The developing step may include a resist heating step for increasing a hardness of the resist films 65c and 65d, or for more securely adhering the resist films 65c and 65d to the elongated metal film 64. The resist heating step is performed in an atmosphere of inert gas such as argon gas, helium gas, nitrogen gas or the like, at a temperature within a range of from 100 to 400° C., for example.

Figure 14B:
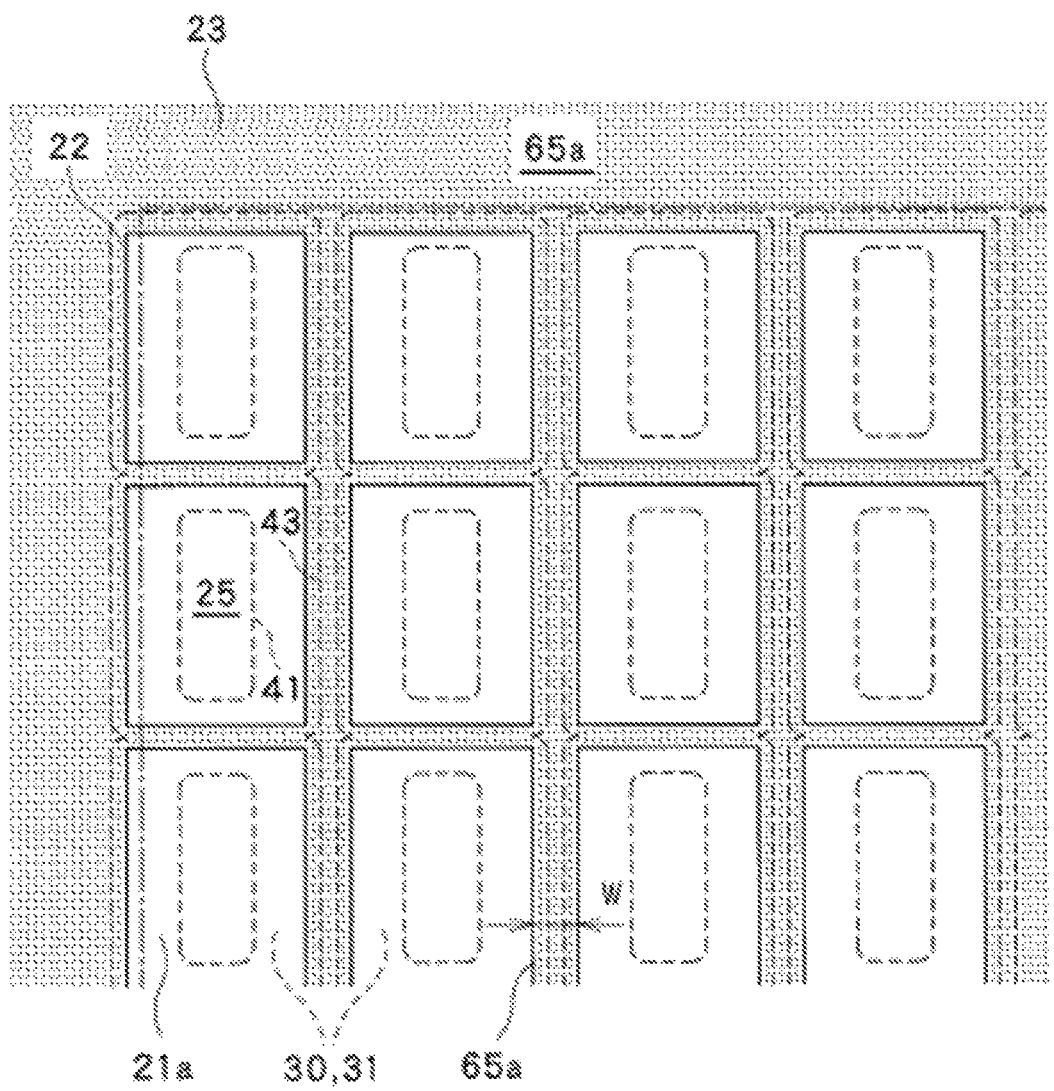
FIG. 14B is a partial plan view when the elongated metal plate shown in FIG. 14A is seen from a first surface side.

FIG. 14B is a partial plan view of the elongated metal plate 64 of FIG. 14A on which the first and second resist patterns 65a and 65b are provided, when seen from the side of the first surface 64a. In FIG. 14B, an area on which the first resist pattern 64a is provided is shaded. In addition, a first recess 30, a wall surface 31, a connection portion 41 and a top portion 43, which are to be formed by the succeeding etching step, are shown by dotted lines.

Figure 15:
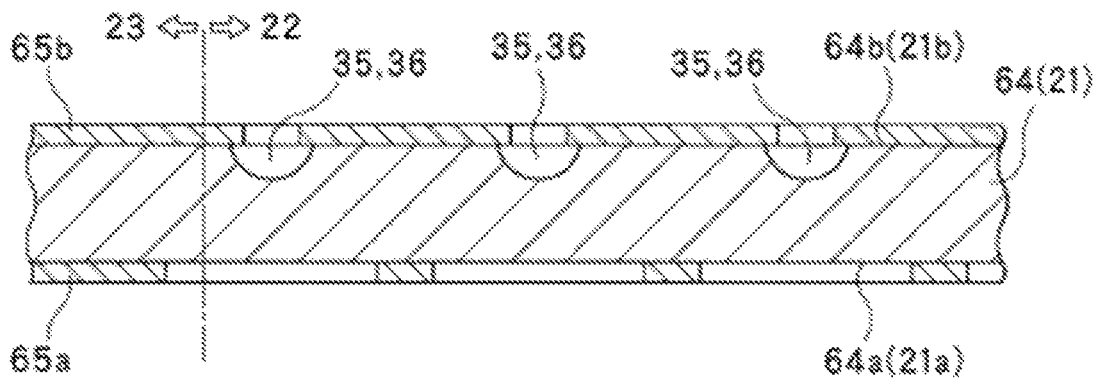
FIG. 15 is a view for explaining an example of the manufacturing method for the deposition mask, showing an elongated metal plate in a section along a normal direction.

Then, as shown in FIG. 15, there is performed a second surface etching step of etching the area of the second surface 64b of the elongated metal plate 64, which is not covered with the second resist pattern 65b, by using a second etchant. For example, the second etchant is ejected from a nozzle, which is disposed on the side facing the second surface 64b of the transported elongated metal plate 64, toward the second surface 64b of the elongated metal plate 64 through the second resist pattern 65b. As a result, as shown in FIG. 15, areas of the elongated metal plate 64, which are not covered with the resist pattern 65b, are eroded by the second etchant. Thus, a lot of second recesses 35 are formed in the second surface 64b of the elongated metal plate 64. The second etchant to be used is an etchant containing ferric chloride solution and hydrochloric acid.

Figure 16:
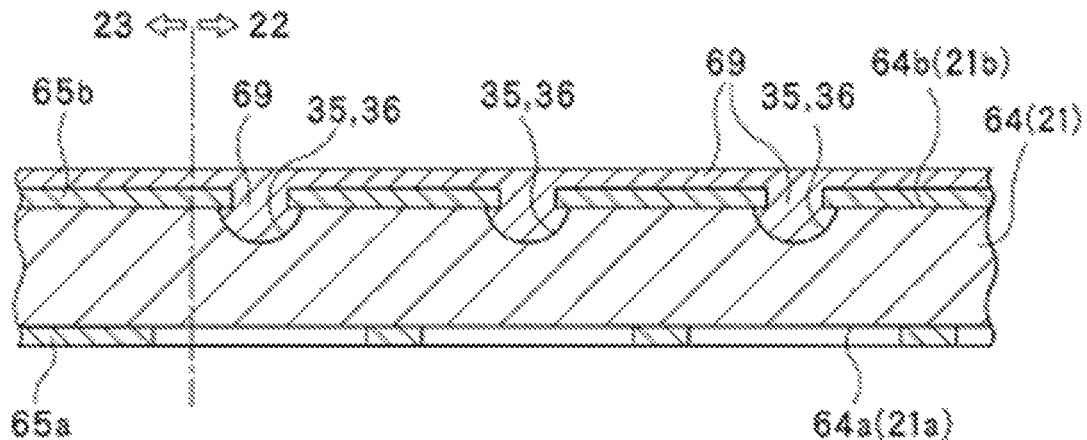
FIG. 16 is a view for explaining an example of the manufacturing method for the deposition mask, showing an elongated metal plate in a section along a normal direction.

After that, as shown in FIG. 16, the second recesses 35 are coated with a resin 69 resistant to a first etchant that is used in a succeeding first surface etching step. Namely, the second recesses 35 are sealed by the resin 69 resistant to the first etchant. In the example shown in FIG. 16, a film of the resin 69 is formed to cover not only the formed second recesses 35 but also the second surface 64b (resist pattern 65b).

Figure 17:
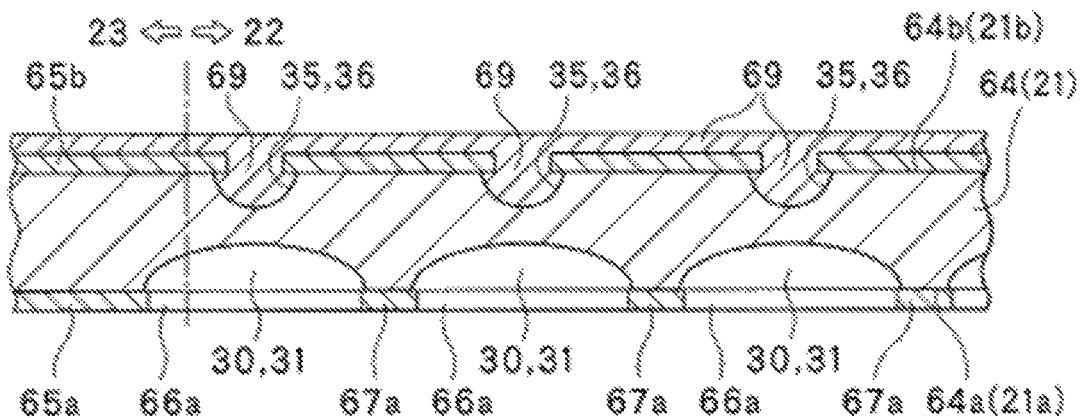
FIG. 17 is a view for explaining an example of the manufacturing method for the deposition mask, showing an elongated metal plate in a section along a normal direction.

Then, as shown in FIG. 17, there is performed the first surface etching step of etching an area of the first surface 64a of the elongated metal plate 64, which is not covered with the first resist pattern 65a, to form a first recess 30 in the first surface 64a. The first surface etching step is performed until each second recess 35 and each first recess 30 communicate with each other so that a through-hole 25 is formed. Similarly to the aforementioned second etchant, the first etchant to be used is an etchant containing ferric chloride solution and hydrochloric acid.

Figure 18:
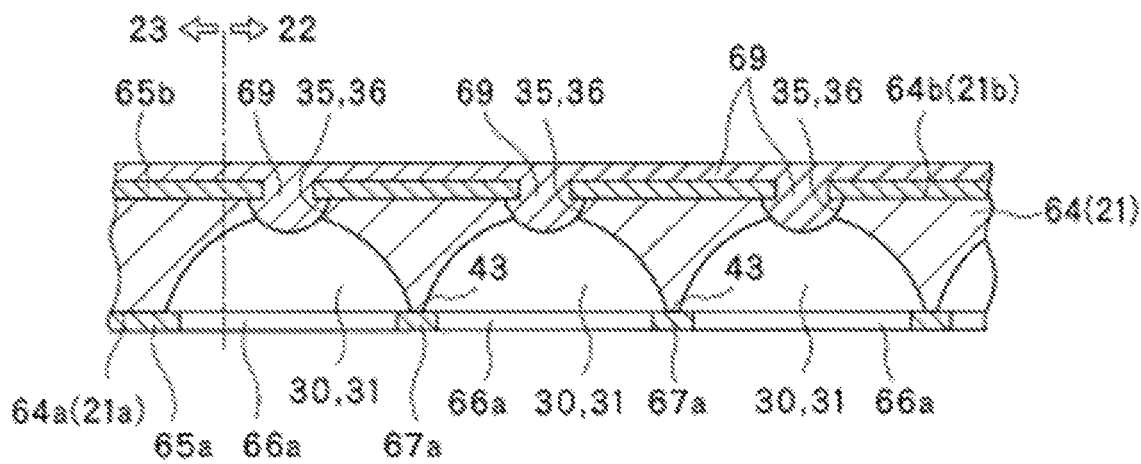
FIG. 18 is a view for explaining an example of the manufacturing method for the deposition mask, showing an elongated metal plate in a section along a normal direction.

The erosion by the first etchant takes place in a portion of the elongated metal plate 64, which is in contact with the first etchant. Thus, the erosion develops not only in the normal direction (thickness direction) of the elongated metal plate 64 but also in a direction along the plate plane of the elongated metal plate 64. Preferably, the first surface etching step is finished before the two first recesses 30, which are respectively formed at positions facing two adjacent holes 66a of the resist pattern 65a, are merged with each other on a reverse side of a bridge portion 67a positioned between the two holes 66a. Thus, as shown in FIG. 18, the aforementioned top portion 43 can be left on the first surface 64a of the elongated metal plate 64.

Figure 19:
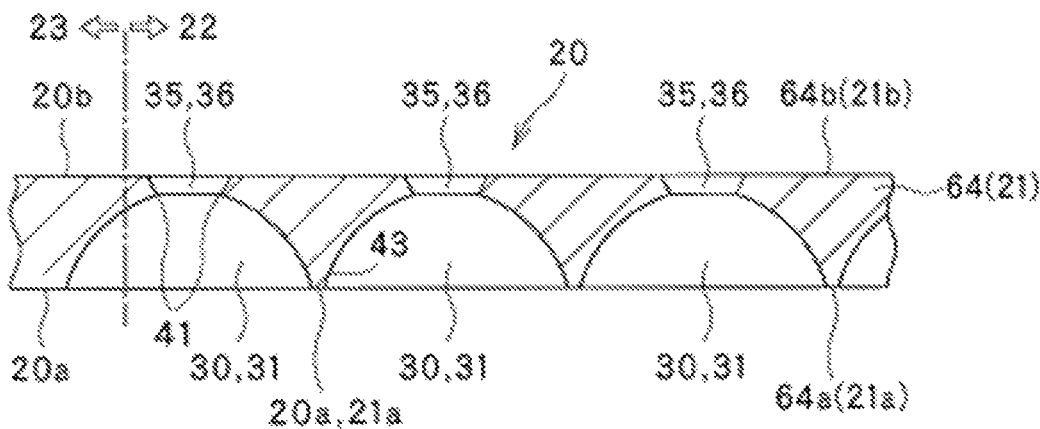
FIG. 19 is a view for explaining an example of the manufacturing method for the deposition mask, showing an elongated metal plate in a section along a normal direction.

After that, as shown in FIG. 19, the resin 69 is removed from the elongated metal plate 64. For example, the resin 69 can be removed by using an alkali-based peeling liquid. When the alkali-based peeling liquid is used, as shown in FIG. 19, the resist patterns 65a and 65b are removed simultaneously with the removal of the resin 69. However, after the removal of the resin 69, the resist patterns 65a and 65b may be removed separately from the resin 69.

The elongated metal plate 64 having a lot of through-holes 25 formed therein in the above manner is transported to a severing apparatus (severing means) 73 by the transport rollers 72, 72 which are rotated while sandwiching therebetween the elongated metal plate 64. The above-described supply core 61 is rotated through a tension (tensile stress) that is applied by the rotation of the transport rollers 72, 72 to the elongated metal plate 64, so that the elongated metal plate 64 is supplied from the winding body 62.

Thereafter, the elongated metal plate 64 in which a lot of through-holes 25 are formed is severed by the severing apparatus (severing means) 73 to have a predetermined length and a predetermined width, whereby the sheet-like metal plates 21 having a lot of through-holes 25 formed therein can be obtained.

In this manner, the deposition mask 20 formed of the metal plate 21 with a lot of through-holes 25 formed therein can be obtained. According to this embodiment, the elongated metal plate 64 from which the metal plate 21 is originated is manufactured such that an existence amount of nickel hydroxide in the first surface 64a satisfies the above condition (1). The aforementioned resist pattern 65a and the resist film 65c from which the resist pattern 65a is originated are attached to such a first surface 64a. Thus, the adhesion force between the first surface 64a of the elongated metal plate 64 and the first resist pattern 65c can be sufficiently ensured. In addition, as the resist film 65c, a so-called dry film having a high resolution, such as a resist film containing an acryl-based photo-setting resin, is used. Thus, according to this embodiment, the first resist pattern 65a of a narrow width can be precisely formed on the first surface 64a of the elongated metal plate 64, while preventing a trouble such as peeling of the first resist pattern 65a from the metal plate 21. Thus, the deposition mask 20 used for producing an organic EL display device having a high pixel density can be manufactured with a high throughput.

In addition, according to this embodiment, since the first resist pattern 65a with a desired width can be precisely formed on the first surface 64a of the elongated metal plate 64, the deposition mask 20 having the top portion 43 with a desired width β can be produced. Thus, the aforementioned angle θ1 can be increased as much as possible, while the deposition mask 20 has a sufficient strength.

(Deposition Step)

Next, there is explained a method for depositing the deposition material onto the substrate 92 by using the obtained deposition mask 20. As shown in FIG. 2, the second surface 20b of the deposition mask 20 is firstly brought into tight contact with the substrate 92. At this time, the second surface 20b of the deposition mask 20 may be brought into tight contact with the surface of the substrate 92, with the use of magnets, not shown. In addition, as shown in FIG. 1, the deposition masks 20 are attached to the frame 15 in a taut state, so that the surface of each deposition mask 20 is in parallel with the surface of the glass substrate 92. Thereafter, by heating the deposition material 98 in the crucible 94, the deposition material 98 is evaporated or sublimated. The evaporated or sublimated deposition material 98 adheres to the substrate 92 through the through-holes 25 in the deposition masks 20. As a result, a film of the deposition material 98 is formed on the surface of the substrate 92 in a desired pattern corresponding to the positions of the through-holes 25 of the deposition masks 20.

According to this embodiment, since the top portion 43 having a desired width β can be left on the side of the first surface 20a, the deposition mask 20 can have a sufficient strength.

The aforementioned embodiment can be variously modified. Herebelow, modification examples are described with reference to the drawings according to need. In the below description and the drawings used in the below description, a part that can be similarly constituted to the above embodiment has the same symbol as that of corresponding part the above embodiment, and overlapped description is omitted. In addition, when the effect obtained by the aforementioned embodiment is apparently obtained in the modification examples, description thereof is possibly omitted.

In the aforementioned embodiment, the "first surface" specified by the aforementioned condition (1) is a surface of the elongated metal plate 64 or the metal plate 21, on which the deposition material 98 is disposed on the deposition step. However, the "first surface" specified by the aforementioned condition (1) may be a surface of the elongated metal plate 64 or the metal plate 21, on which the substrate 92 is disposed. In this case, a resist pattern to be attached to the side of the elongated metal plate 64 or the metal plate 21, on which the substrate 92 is disposed, can be securely adhered to the elongated metal plate 64 or the metal plate 21. Thus, recesses can be precisely formed on the side of the elongated metal plate 64 or the metal plate 21, on which the substrate 92 is disposed, with a high throughput.

Namely, in this embodiment, the aforementioned condition (1) can be said as below.

"When a composition analysis of at least a surface of one surface of a metal plate and the other surface located oppositely to the one surface is performed by using the X-ray photoelectron spectroscopy, a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide."

In addition, according to this embodiment, when the result of the composition analysis of at least a surface of one surface of the metal plate and the other surface thereof located oppositely to the one surface satisfies the aforementioned condition, recesses can be precisely formed in the surface of the meal plate with a high throughput.

In addition, the condition in which "a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide" may be satisfied by both the first surface 64a and the second surface 64b of the metal plate 64.

Figure 20:
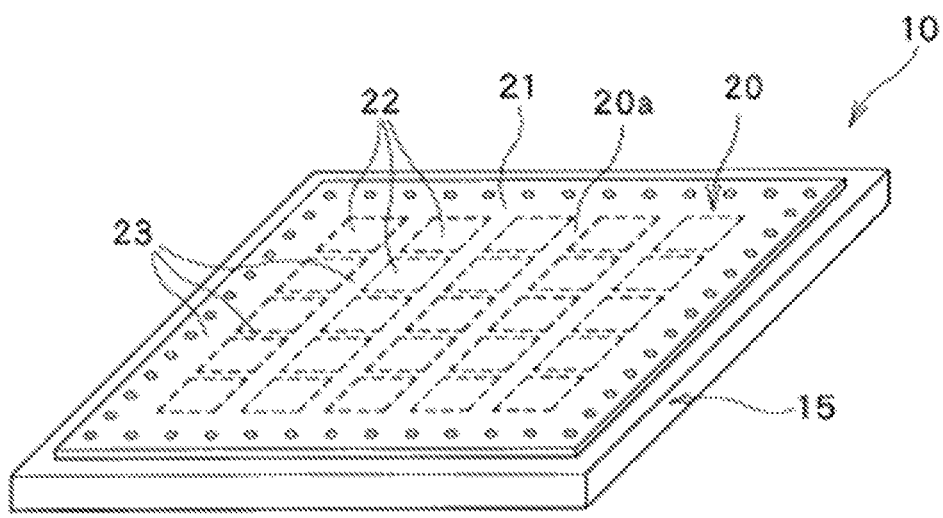
FIG. 20 is a view showing a modification example of the deposition mask apparatus including a deposition mask.

In addition, in the aforementioned embodiment, a plurality of the deposition masks 20 are assigned in the width direction of the elongated metal plate 64. In addition, in the deposition step, the plurality of deposition masks 20 are mounted on the frame 15. However, not limited thereto, as shown in FIG. 20, there may be used deposition masks 20 having a plurality of the effective areas 22 arranged like a grid along both the width direction and the longitudinal direction of the metal plate 21.

In addition, in the aforementioned embodiment, the resist heating step is performed in the developing step. However, when the elongated metal plate 64 is manufactured to satisfy the aforementioned condition (1) whereby the adhesion force between the elongated metal plate 64 and the resist film 65c can be sufficiently ensured, the resist heating step may be omitted. When the resist heating step is not performed, the hardness of the first resist pattern 65a is lower than a case in which the resist heating step is performed. Thus, after the through-holes 25 have been formed, the resist pattern 65a can be more easily removed.

In addition, in the aforementioned embodiment, a metal plate having a desired thickness is obtained by rolling a base metal to produce a plate member, and then by annealing the plate member. However, not limited thereto, a metal plate having a desired thickness may be manufactured by a foil creating step utilizing a plating process. In the foil creating step, for example, while a drum made of stainless, which is partially immersed in a plating liquid, is rotated, a plating film is formed on a surface of the drum. By peeling off the plating film, an elongated metal plate can be manufactured in a roller-to-roller manner. When a metal plate is manufactured of an iron alloy containing nickel, a mixture solution of a solution containing a nickel compound and a solution of an iron compound may be used as a plating liquid. For example a mixture solution of a solution containing nickel sulfamate and a solution containing iron sulfamate may be used, for example. An additive such as malonic acid or saccharin may be contained in the plating liquid.

Then, the aforementioned annealing step may be performed to the metal plate obtained in this manner. In addition, after the annealing step, there may be performed the aforementioned severing step of severing both ends of the metal plate, so as to adjust the width of the metal plate into a desired width.

Also when a metal plate is produced by utilizing a plating process, by performing the step of forming the resist patterns 65a and 65b and the step of etching the first surface and the second surface of the metal plate, the deposition mask with the plurality of through-holes 25 formed therein can be obtained, similarly to the aforementioned embodiment. In addition, the use of the condition (1) can optimize the judgment of a metal plate and manufacturing conditions.

EXAMPLES

Next, the present invention is described in more detail based on examples, and the present invention is not limited to the below description of the examples unless the present invention departs from its spirit.

Example 1

(First Winding Body)

A base metal made of an iron alloy containing 34 to 38 mass % of nickel, chrome, balancing iron and unavoidable impurities was prepared. Then, the base metal was subjected to the rolling step, the slitting step and the annealing step, which are described above, so that a winding body (first winding body) around which an elongated metal plate having a thickness of 20 μm was wound was manufactured.

[Composition Analysis]

After that, the elongated metal plate 64 was cut out by using a shear into a predetermined range, e.g., 30×30 mm, so as to obtain a first specimen. Then, a composition of a surface of the first specimen was analyzed by means of the XPS method. As a measuring apparatus, an XPS apparatus ESCALAB 220i-XL manufactured by Thermo Fisher Scientific Company was used.

The XPS apparatus was set as follows upon the composition analysis.

Incident X-ray: monochromated Al kα (monochromated X-ray, hv=1486.6 eV)

X-ray output: 10 kV·16 mA (160 W)

Aperture opening degree: F.O.V.=open, A.A.=open

Measured area: 700 μmø

X-ray incident angle ø1 (see FIG. 10): 45 degrees

Photoelectron acceptance angle: 90 degrees

Figure 21A:
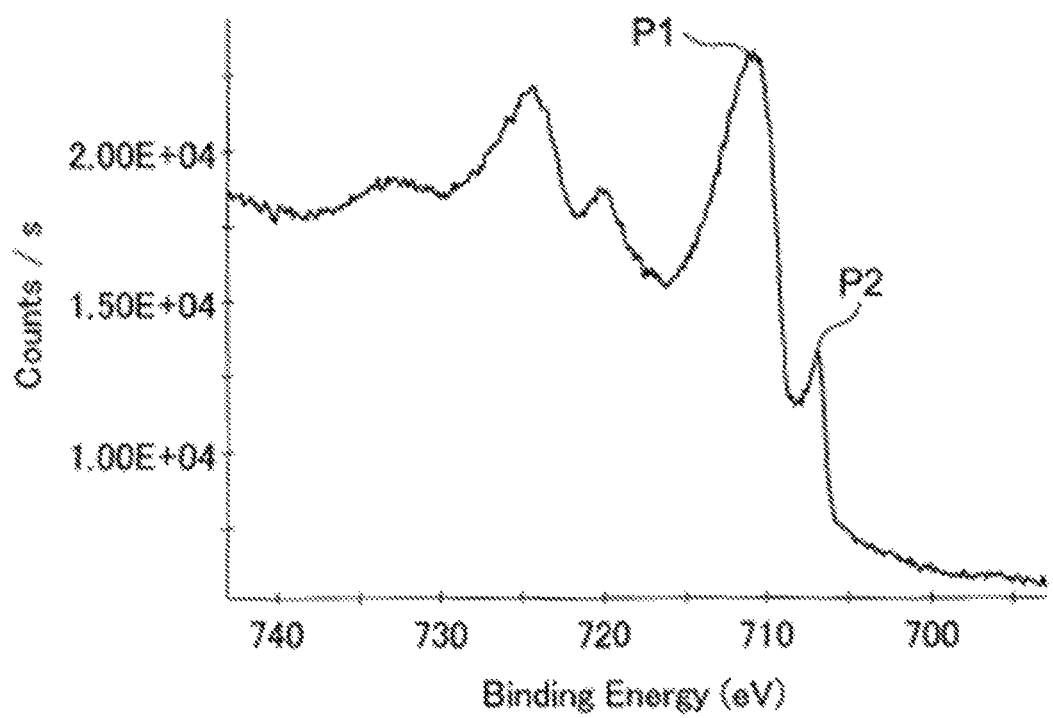
FIGS. 21(a) and 21(b) are views showing a result of analyzing a first specimen cut out from a first winding body by using an XPS apparatus.
Figure 21B:
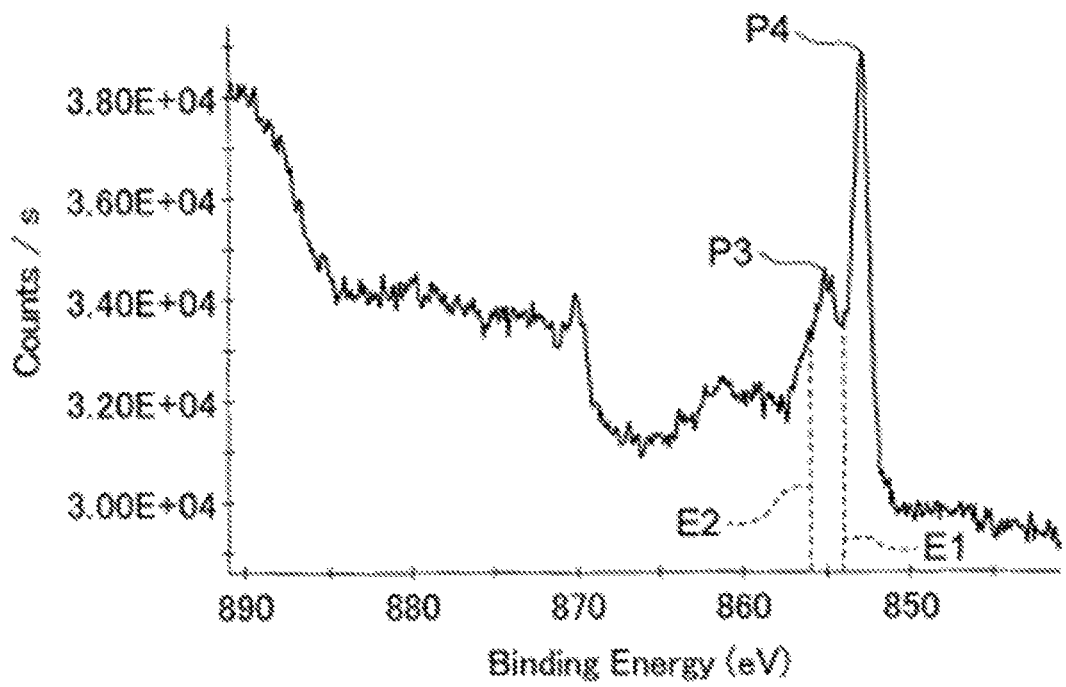

FIGS. 21(a) and 21(b) show results of analysis of the first specimen cut out from the first winding body by means of the XPS apparatus. In FIGS. 21(a) and 21(b), the axis of abscissa shows a photoelectron binding energy (Binding Energy) of an electron orbit of the first specimen, which corresponds to an intensity photoelectrons observed from the first specimen, and the axis of coordinate shows an intensity of the photoelectrons observed from the first specimen. FIG. 21(a) shows a case in which the value of the axis of abscissa is about 700 to 740 eV, and FIG. 21(b) shows a case in which the value of the axis of abscissa is about 850 to 890 eV.

In the composition analysis using the XPS method, a peak which corresponds to a content of a constituent element contained in the first specimen appears at a given position corresponding to the constituent element in the axis of abscissa. For example, in FIG. 21(a), a peak indicated by the symbol P1 corresponds to iron oxide and iron hydroxide contained in the first specimen, and a peak indicated by the symbol P2 corresponds to iron contained in the first specimen. In addition, in FIG. 21(b), a peak indicated by the symbol P3 corresponds to nickel oxide and nickel hydroxide contained in the first specimen, and a peak indicated by the symbol P4 corresponds to nickel contained in the first specimen.

Figure 22A:
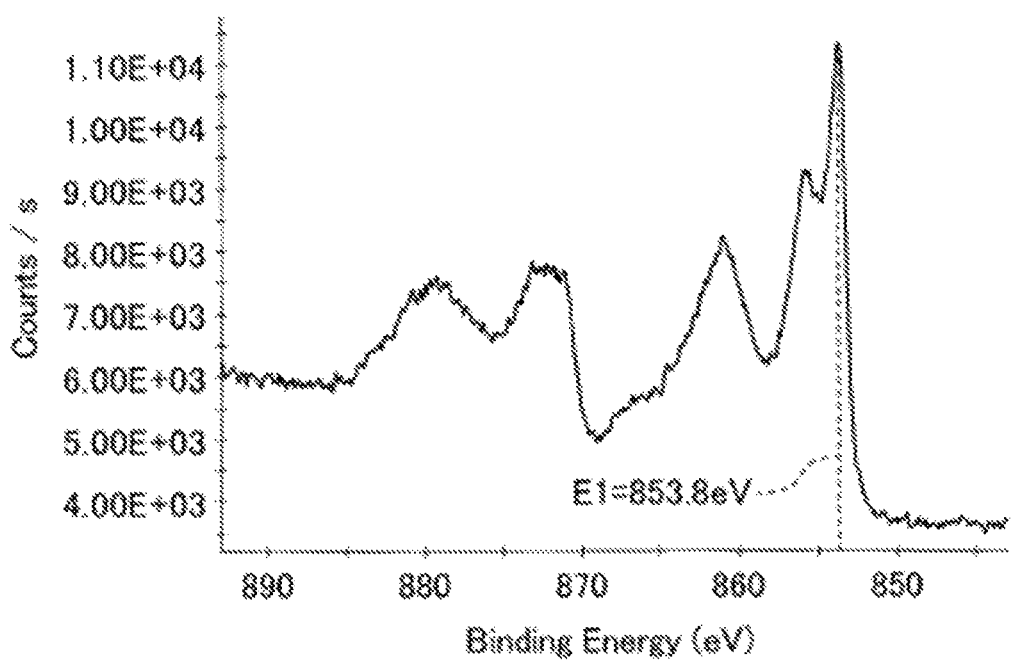
FIG. 22(a) is a view showing a result of analyzing nickel oxide, prepared as a first reference specimen, by using an XPS method.
Figure 22B:
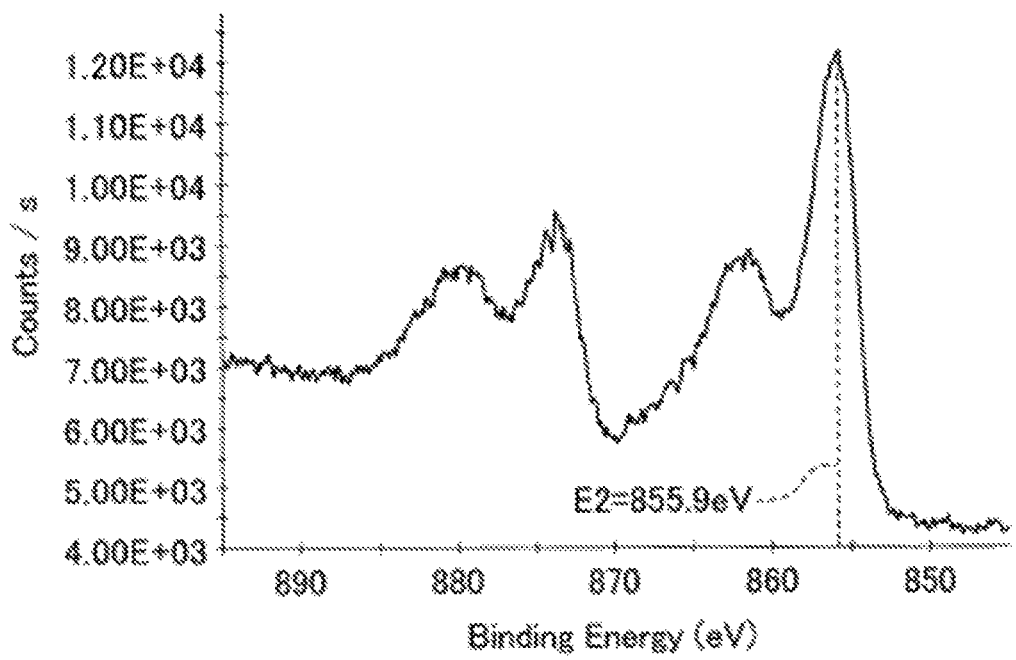
FIG. 22(b) is a view showing a result of analyzing nickel hydroxide, prepared as a second reference specimen, by using the XPS method.

As a reference, FIG. 22(a) shows a result of analyzing nickel oxide (NiO), which was prepared as a first reference specimen, by means of the XPS method. In addition, FIG. 22(b) shows a result of analyzing nickel hydroxide (Ni(OH)$_2$), which was prepared as a second reference specimen, by means of the XPS method. As shown in FIG. 22(a), a peak corresponding to nickel oxide appears at a position where the axis of abscissa value is a first value E1=853.8 eV. On the other hand, as shown in FIG. 22(b), a peak corresponding to nickel hydroxide appears at a position where the axis of abscissa value is a second value E2=855.9 eV.

In FIG. 21(b), as a reference, a position of the first value E1 at which the peak corresponding to nickel oxide appears, and a position of the second value E2 at which the peak corresponding to the nickel hydroxide appears are shown by the dotted lines. Since the values of E1 and E2 are close to each other, as shown in FIG. 21(b), in the measurement result of the first specimen, the peak P3 includes both a detection result of photoelectrons corresponding to nickel oxide and a detection result of photoelectrons corresponding to nickel hydroxide. It is not easy to accurately separate the peak P3 shown in FIG. 21(b) into a peak corresponding to nickel oxide and a peak corresponding to nickel hydroxide.

In consideration of this point, in the aforementioned condition (1), an adhesion force between the metal plate and the resist pattern is evaluated by using a value which is a sum of the detection result of photoelectrons corresponding to nickel oxide and the detection result of photoelectrons corresponding to nickel hydroxide.

After the peaks P1 to P4 shown in FIGS. 21(a) and 21(b) had been measured, peak planar dimension values were calculated by integrating the planar dimensions of the respective peaks. The results were: the peak planar dimension value of the peak P1 corresponding to the iron oxide and iron hydroxide was 22329.3, the peak planar dimension value of the peak P2 corresponding to iron was 4481.8, the peak planar dimension value of the peak P3 corresponding to the nickel oxide and nickel hydroxide was 9090.5, and the peak planar dimension value of the peak P4 corresponding to nickel was 4748.9. Thus, when a sum of the peak planar dimension value of nickel oxide and the peak planar dimension value of nickel hydroxide is represented as A1, and a sum of the peak planar dimension value of iron oxide and the peak planar dimension value of iron hydroxide is represented as A2, A1/A2=0.41. Thus, it can be said that the first winding body from which the first specimen was taken out does not satisfy the aforementioned condition (1).

The peak planar dimension values of the respective peaks P1 to P4 were calculated by means of an analysis function of the XPS apparatus. In order to prevent that a measuring result varies depending on an analyzer, the Shirley method was always employed as a background calculating method.

A method for calculating the above A1/A2 based on the analysis result by means of the XPS method is described in detail herebelow.

1. Adjustment of XPS Apparatus

Firstly, adjustment of a spectrograph energy axis of the XPS was performed to satisfy the following adjustment conditions 1 to 3.

Adjustment condition 1: Ag $3d_{5/2}$ 368.26±0.05 eV
Adjustment condition 2: Au $4f_{7/2}$ 83.98±0.05 eV
Adjustment condition 3: Cu $2p_{3/2}$ 932.67±0.05 eV The adjustment condition 1 means that the spectrograph energy axis was adjusted such that a photoelectron binding energy obtained based on a silver $3d_{5/2}$ orbit was within a range of 368.26±0.05 eV. Similarly, the adjustment condition 2 means that the spectrograph energy axis was adjusted such that a photoelectron binding energy obtained based on a gold $4f_{7/2}$ orbit was within a range of 83.98±0.05 eV. Similarly, the adjustment condition 3 means that the spectrograph energy axis was adjusted such that a photoelectron binding energy obtained based on a copper $2p_{3/2}$ orbit was within a range of 932.67±0.05 eV.

In addition, a charge-up correction of the XPS apparatus was set such that a photoelectron biding energy obtained based on C—C bond of a carbon is orbit was within a range of 284.7 to 285.0 (eV).

After that, a specimen made of an iron-nickel alloy was analyzed by means of the XPS apparatus as adjusted above, and the aforementioned A1/A2 was calculated. A method for calculating the aforementioned A2 based on the peaks P1 and P2 on iron is firstly described with reference to FIGS. 27A to 27D.

2. Analysis on Iron

Figure 27A:
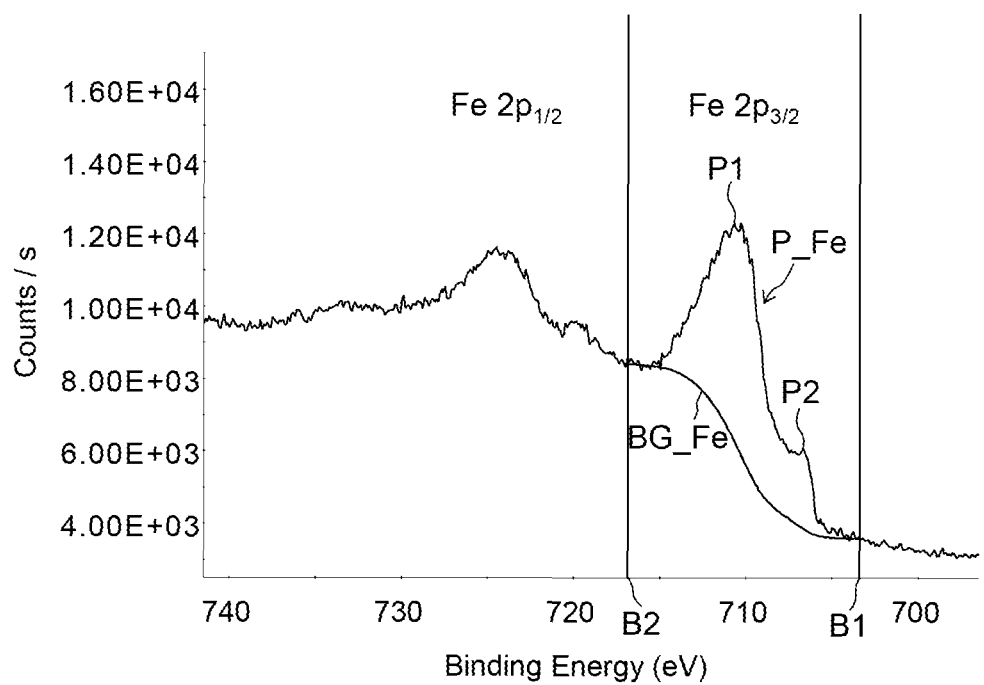
FIG. 27A is a view showing a step of calculating a background line of an iron total peak on iron $2P_{3/2}$ orbit.

FIG. 27A shows in enlargement a result of analyzing a certain specimen made of an iron-nickel alloy by means of the XPS apparatus, in particular, a result in which an axis of abscissa value is within a range of from 700 to 740 eV. As shown in FIG. 27A, the result in which the axis of abscissa value is within a range of from 700 to 740 eV includes a graph showing an intensity distribution of photoelectrons obtained based on an iron $2p_{1/2}$ orbit, and a graph showing an intensity distribution of photoelectrons obtained based on an iron $2p_{3/2}$ orbit. Herein, there is described an example in which the aforementioned A2 was calculated based on the graph showing an intensity distribution of photoelectrons obtained based on an iron $2p_{3/2}$ orbit (referred to as "iron total peak P_Fe" herebelow).

[Calculating Step of Background Line]

A step of calculating a background line BG_Fe in the iron total peak P_Fe is firstly described. A lower limit value B1 and an upper limit value B2 of values of a photoelectron binding energy of the axis of abscissa in the $2p_{3/2}$ orbit of iron to be analyzed were determined as follows.

Lower limit value B1: 703.6±0.2 eV
Upper limit value B2: 717.0±0.2 eV

Then, a background line BG_Fe in the iron total peak P_Fe within the range of from the lower limit value B1 to the upper limit value B2 was calculated by using the Shirley method. The "±0.2 eV" in the above lower limit value B1 and the upper limit value B2 means that values of the lower limit value B2 and the upper limit value B2 were slightly adjusted for each specimen, in order that noises of a measurement result did not affects a calculation result of the background line BG_Fe.

[Separation Step of Peak on Iron Alone]

Figure 27B:
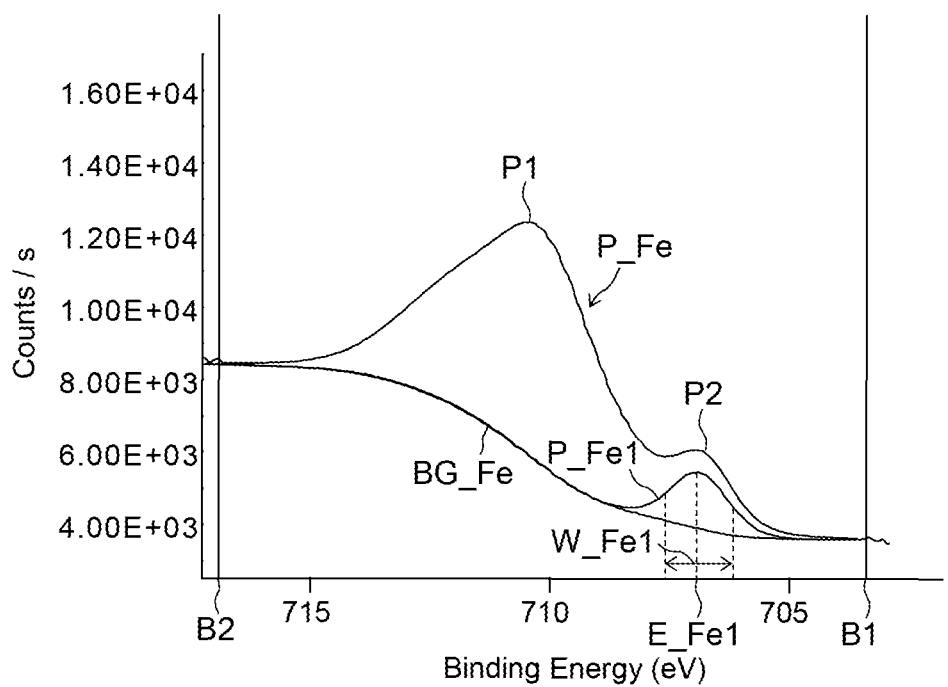
FIG. 27B is a view showing a step of separating a peak on iron alone from the iron total peak.

Next, a step of separating a peak on iron alone from the iron total peak P_Fe is described in FIG. 27B. FIG. 27B is a view showing in enlargement the iron total peak P_Fe shown in FIG. 27A. Herein, there is explained a result of separating the peak on iron alone from the iron total peak P_Fe after the iron total peak P_Fe was subjected to a smoothing process. As the smoothing method, a known method such as averaging or the like may be employed.

A peak position E_Fe1 of a peak on iron alone was firstly determined. To be specific, it was determined whether a peak that appeared in relation to iron alone was the peak P1 or P2 included in the iron total peak P_Fe. In the field of XPS method, it is known that a photoelectron binding energy based on a $2p_{3/2}$ orbit of iron alone is about 707 eV. Thus, the peak P2 was identified as the peak that appeared in relation to iron alone. Then, a position of the peak P2 was searched. When a peak position of the peak P2 was within a range of 706.9±0.2 eV, the position of the peak P2 was employed as the peak position E_Fe1 of the peak on iron alone.

Then, a half-value width W_Fe1 of the peak on iron alone was set at 1.54 eV. Thereafter, by using the analysis function of the XPS apparatus, a peak whose peak position was E_Fe1 and whose half-value width was W_Fe1 was separated from the iron total peak P_Fe. In FIG. 27B, the thus obtained peak on iron alone is indicated by the symbol P_Fe1. In the analysis by the XPS apparatus, there is a possibility that a half-value width of the obtained peak P_Fe1 varies from the set half-value width W_Fe1. In this case, variation within a range of ±0.1 eV was allowed.

In the terms related to the iron total peak P_Fe, the aforementioned "peak P_Fe1 on iron alone" and the below described "peak P_Fe2" and "peak P_Fe3" are peaks obtained by resolving the iron total peak P_Fe into a plurality of peaks based on an element alone and a compound contained in a specimen Namely, the aforementioned "peaks P1 and P2" are peaks discriminated by the shape of the iron total peak P_Fe, and "peaks P_Fe1, P_Fe2 and P_Fe3" are peaks obtained by resolving the iron total peak P_Fe based on a physical theory.

[Calculating Step of Peak Planar Dimension on Iron Alone]

Then, a planar dimension S_Fe1 of the peak P_Fe1 of iron alone was calculated. The planar dimension S_Fe1 is a planar dimension of an area (hatched area) surrounded by the peak P_Fe1 and the background line BG_Fe in FIG. 27C In addition, a planar dimension of the iron total peak P_Fe was calculated. The planar dimension of the iron total peak P_Fe is a planar dimension of an area surrounded by the iron total peak P_Fe and the Background line BG_Fe in FIG. 27C.

Figure 27C:
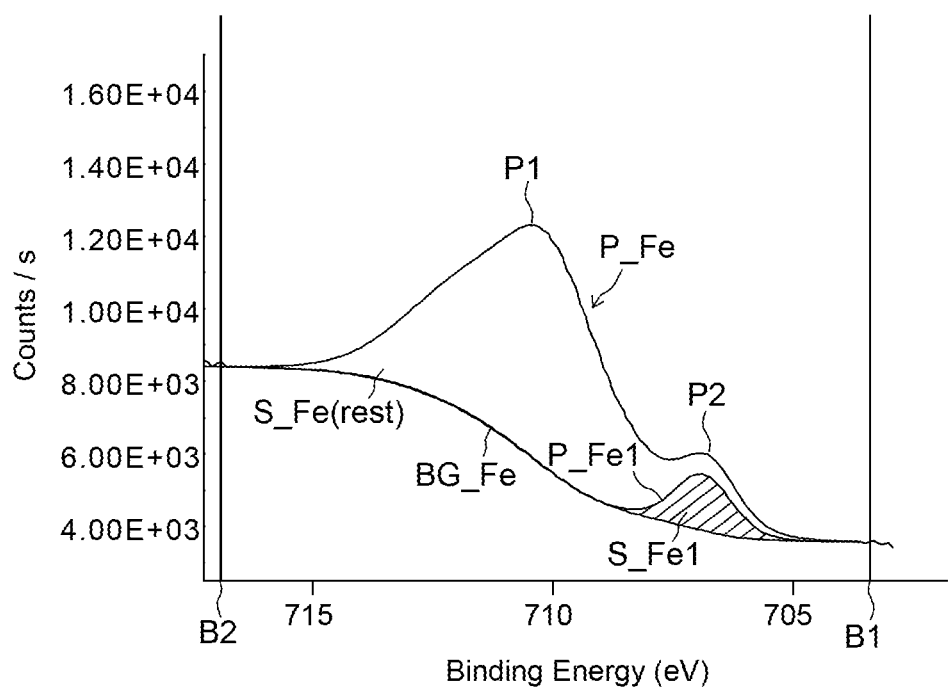
FIG. 27C is a view showing a step of calculating a peak area on iron alone.

Then, a planar dimension S_Fe (REST) shown in FIG. 27C was calculated by subtracting the planar dimension S_Fe1 of the peak P_Fe1 on iron alone from the planar dimension of the iron total peak P_Fe. The planar dimension S_Fe (REST) as calculated above was used as the aforementioned A2, i.e., the sum of the peak planar dimension value of iron oxide and the peak planar dimension value of iron hydroxide.

Figure 27D:
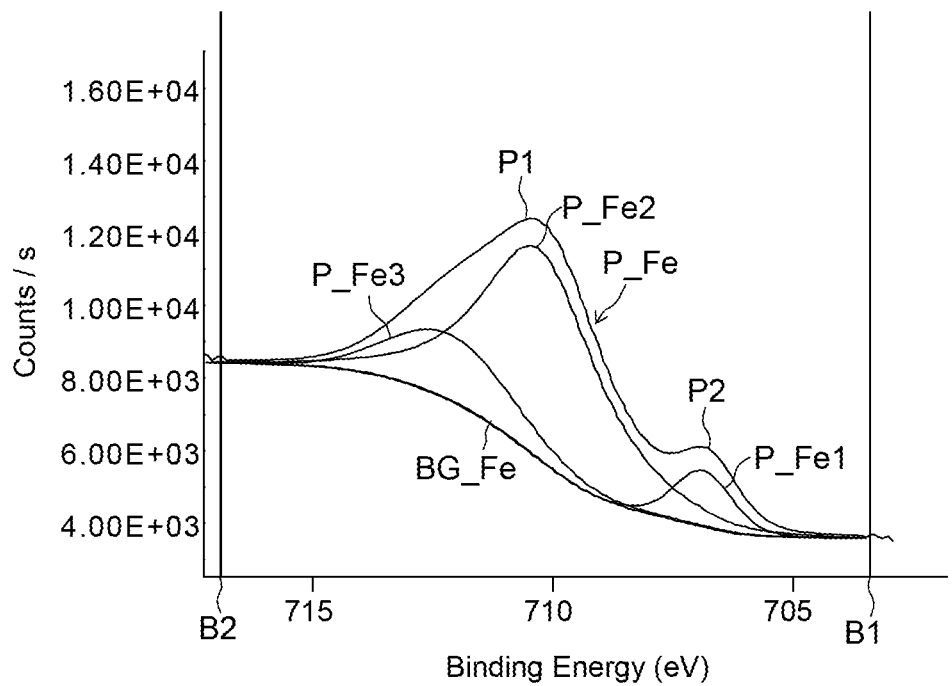
FIG. 27D is a view showing as a reference a result of separating peaks on iron oxide and iron hydroxide.

For the purpose of reference, FIG. 27D shows a result of separating the total peak P_Fe on the assumption that the iron total peak P_Fe includes the following three peaks, i.e., the peak P_Fe1, the peak P_Fe2 and the peak P_Fe3. As described above, the peak P_Fe1 is a peak on iron alone. In addition, the peak P_Fe2 and the peak P_Fe3 are a peak on iron oxide and a peak on iron hydroxide.

When the iron total peak P_Fe is separated into a plurality of peaks as shown in FIG. 27D, the aforementioned planar dimension S_Fe (REST) corresponds to a total sum of the peak planar dimensions except the peak P_Fe1 on iron alone. Namely, the planar dimension S_Fe (REST) corresponds to the sum of the peak planar dimension of iron oxide and the peak planar dimension value of the iron hydroxide.

Although the position at which a peak on iron alone has been already known, there are a plurality of positions about iron oxide and iron hydroxide. Thus, a peak on iron oxide and a peak on iron hydroxide do not necessarily appear like the two peaks (peak P_Fe2 and peak P_Fe3) shown in FIG. 27. Thus, it is difficult to accurately calculate a rate of iron oxide or iron hydroxide in a surface layer of a specimen. Taking this point into consideration, the sum of the peak planar dimension of iron oxide and peak planar dimension value of iron hydroxide is employed as the aforementioned A2.

The planar dimension S_Fe1 of the peak P_Fe1 on iron alone is sometimes referred to as a planar dimension value of the peak P2, and the planar dimension S_Fe (REST) is sometimes referred to as a planar dimension value of the peak P1.

3. Analysis on Nickel

Figure 28A:
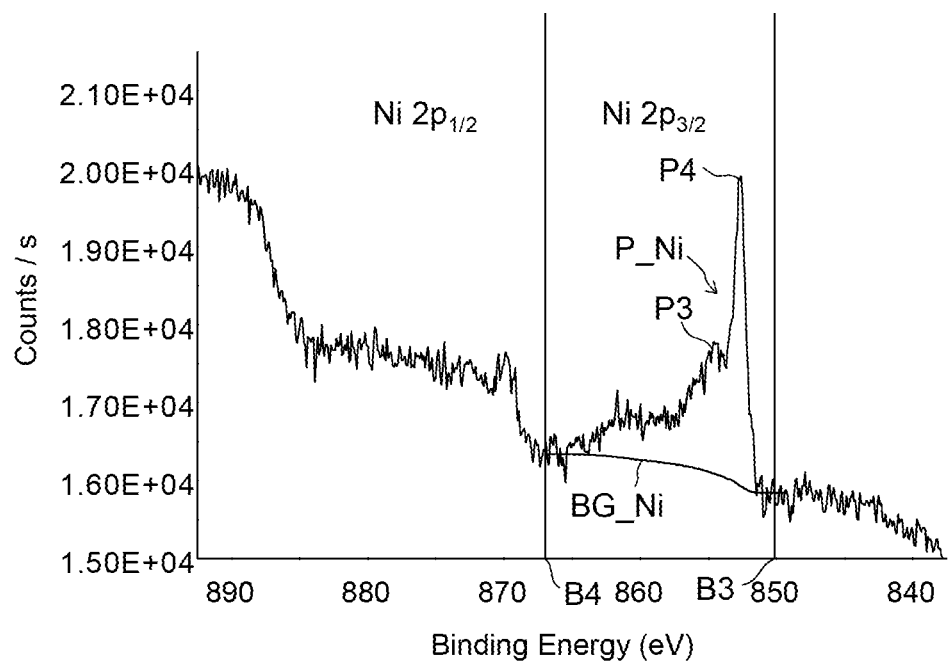
FIG. 28A is a view showing a step of calculating a background line of a total peak on nickel $2P_{3/2}$ orbit.

Next, analysis on nickel is described. FIG. 28A shows in enlargement a result of analyzing a certain specimen made of an iron-nickel alloy by means of the XPS apparatus, in particular, a result in which an axis of abscissa value is in the range of from 850 to 890 eV. As shown in FIG. 28A, the result in which an axis of abscissa value is in the range of from 850 to 890 eV includes a graph showing an intensity distribution of photoelectrons obtained based on a nickel $2p_{1/2}$ orbit, and a graph showing an intensity distribution of photoelectrons obtained based on a nickel $2p_{3/2}$ orbit. Herein, there is described an example in which the aforementioned A1 was calculated based on the graph showing an intensity distribution of photoelectrons obtained based on a nickel $2p_{3/2}$ orbit (referred to as "nickel total peak P_Ni" herebelow). About a process in the method for calculating A1, which is similar to that of the calculating method for A2 for iron, detailed description thereof is omitted.

[Calculating Step of Background Line]

A background line BG_Ni in the nickel total peak P_Ni was calculated by using the Shirley method. A lower limit value B3 and an upper limit value B4 of values of a photoelectron binding energy of the axis of abscissa in the $2p_{3/2}$ orbit of nickel to be analyzed were determined as follows.

Lower limit value B3: 849.5±0.2 eV
Upper limit value B4: 866.9±0.2 eV

[Separation Step of Peak on Nickel Alone]

Figure 28B:
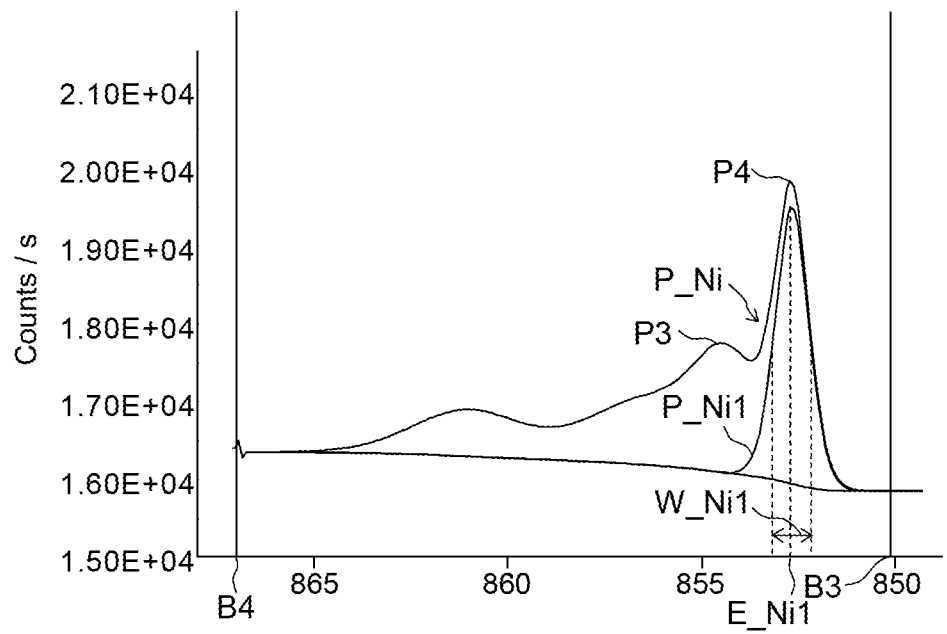
FIG. 28B is a view showing a step of separating a peak on nickel alone from the nickel total peak.

Then, as shown in FIG. 28B, a peak on nickel alone was separated from the nickel total peak P_Ni. To be specific, in the nickel total peak P_Ni, a peak position of the peak P4 that appeared in relation to nickel alone was searched. When a peak position of the peak P4 is within a range of 852.6±0.2 eV, the position of the peak P4 was employed as the peak position E_Ni1 of the peak on nickel alone.

Then, a half-value width W_Ni1 of the peak on nickel alone was set at 1.15 eV. Thereafter, by using the analysis function of the XPS apparatus, a peak whose peak position was E_Ni1 and whose half-value width was W_Ni1 was separated from the nickel total peak P_Ni. In FIG. 28B, the thus obtained peak on nickel alone is indicated by the symbol P_Ni1.

[Calculating Step of Peak Planar Dimension on Nickel Alone]

Then, a planar dimension S_Ni1 of the peak P_Ni1 of nickel alone was calculated. The planar dimension S_Ni1 is a planar dimension of an area (hatched area) surrounded by the peak P_Ni1 and the background line BG_Ni in FIG. 28C.

In addition, a planar dimension of the nickel total peak P_Ni was calculated. The planar dimension of the nickel total peak P_Ni is a planar dimension of an area surrounded by the nickel total peak P_Ni and the background line BG_Ni in FIG. 28C.

Figure 28C:
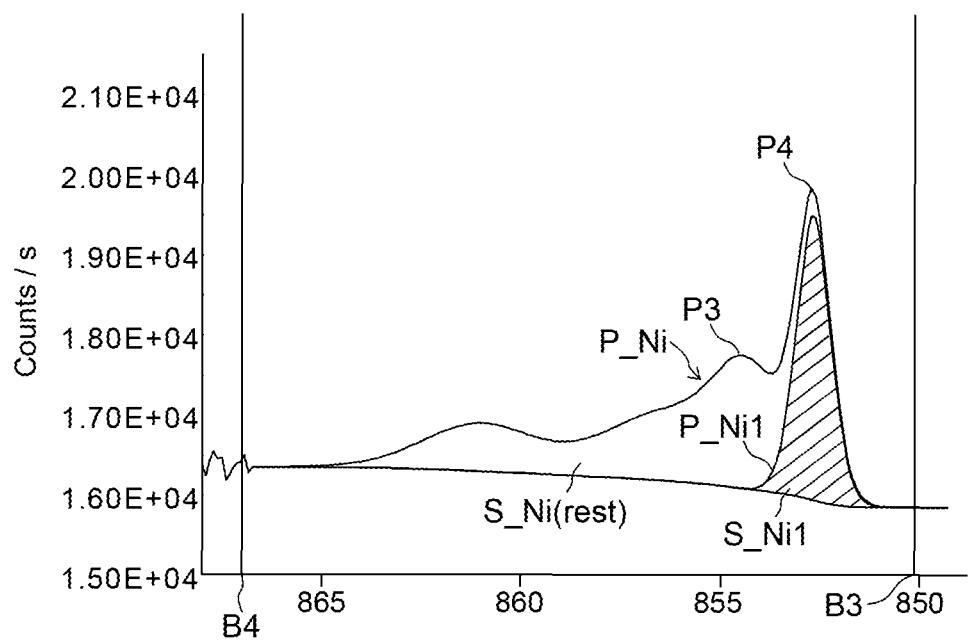
FIG. 28C is a view showing a step of calculating a peak area on nickel alone.

Then, a planar dimension S_Ni (REST) shown in FIG. 28C was calculated by subtracting the planar dimension S_Ni1 of the peak P_Ni of nickel alone from the planar dimension of the nickel total peak P_Ni. The planar dimension S_Ni (REST) as calculated above was used as the aforementioned A1, i.e., the sum of the peak planar dimension value of nickel oxide and the peak planar dimension value of nickel hydroxide.

Figure 28D:
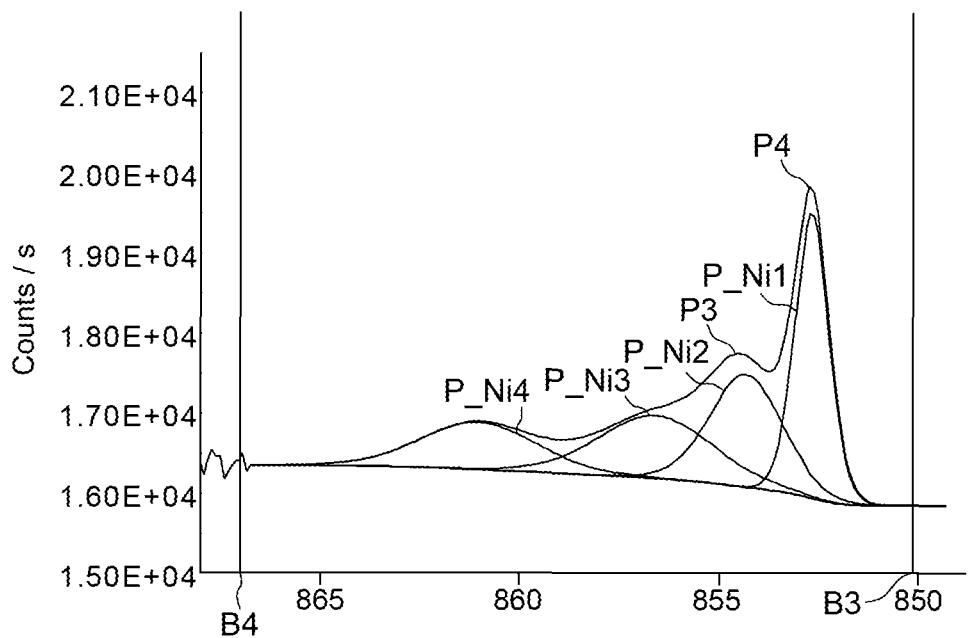
FIG. 28D is a view showing as a reference a result of separating peaks on nickel oxide and nickel hydroxide.
Figure 29:
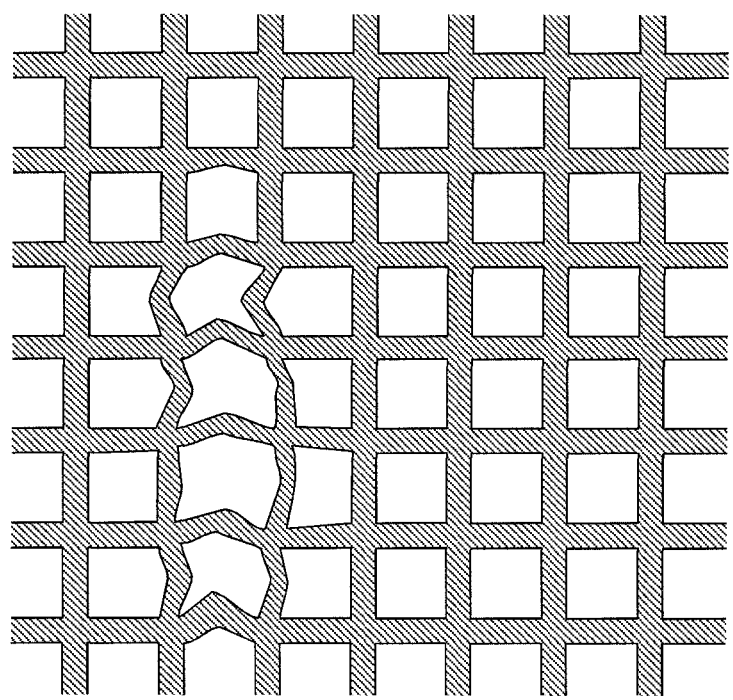
FIG. 29 is a view showing an example in which a part of resist pattern peels off from a metal plate in a developing solution.

For the purpose of reference, FIG. 28D shows a result of separating the total peak P_Ni of nickel into the following four peaks, i.e., the peak P_Ni1, the peak P_Ni2, the peak P_Ni3 and the peak P_Ni4. As described above, the peak P_Ni1 is a peak on nickel alone. In addition, the peak P_Ni2, the peak P_Ni3 and the peak P_Ni4 are peaks on nickel oxide or peaks on nickel hydroxide.

When the nickel total peak P_Ni is separated into the plurality of peaks as shown in FIG. 28D, the aforementioned planar dimension S_Ni (REST) corresponds to a total sum of the peak planar dimensions except the peak P_Ni1 on nickel alone. Namely, the planar dimension S_Ni (REST) corresponds to the sum of the peak planar dimension of nickel hydroxide and the peak planar dimension value of nickel hydroxide.

The planar dimension S_Ni1 of the peak P_Ni1 on nickel alone is sometimes referred to as a planar dimension value of the peak P4, and the planar dimension S_Ni (REST) is sometimes referred to as a planar dimension value of the peak P3.

4. Calculation of A1/A2

A1/A2 was calculated based on the A1 and A2 as calculated above.

[Evaluation on Adhesion Property to Resist Pattern]

Figure 23:
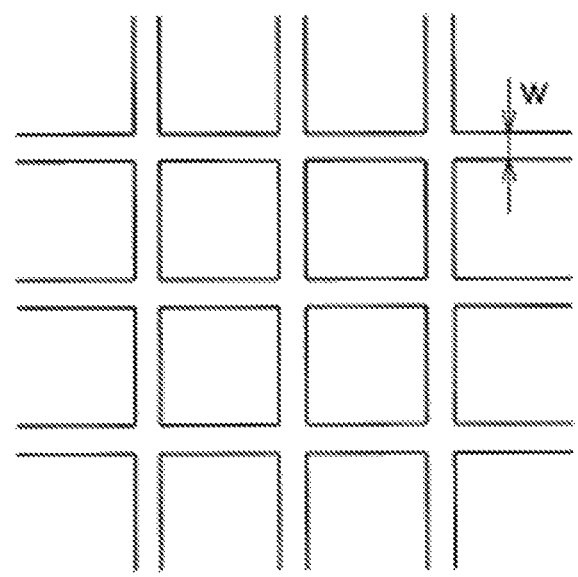
FIG. 23 is a view showing a resist pattern formed on a surface of a first sample.
Figure 24A:
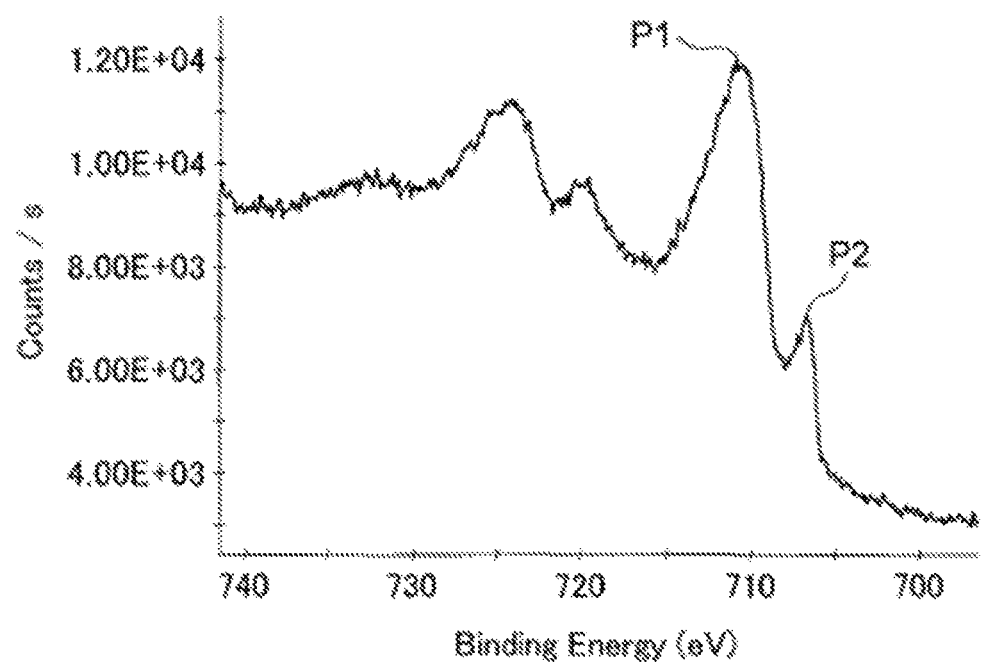
FIGS. 24(a) and 24(b) are views each showing a result of analyzing a second specimen cut out from a second winding body, by using an XPS apparatus.
Figure 24B:
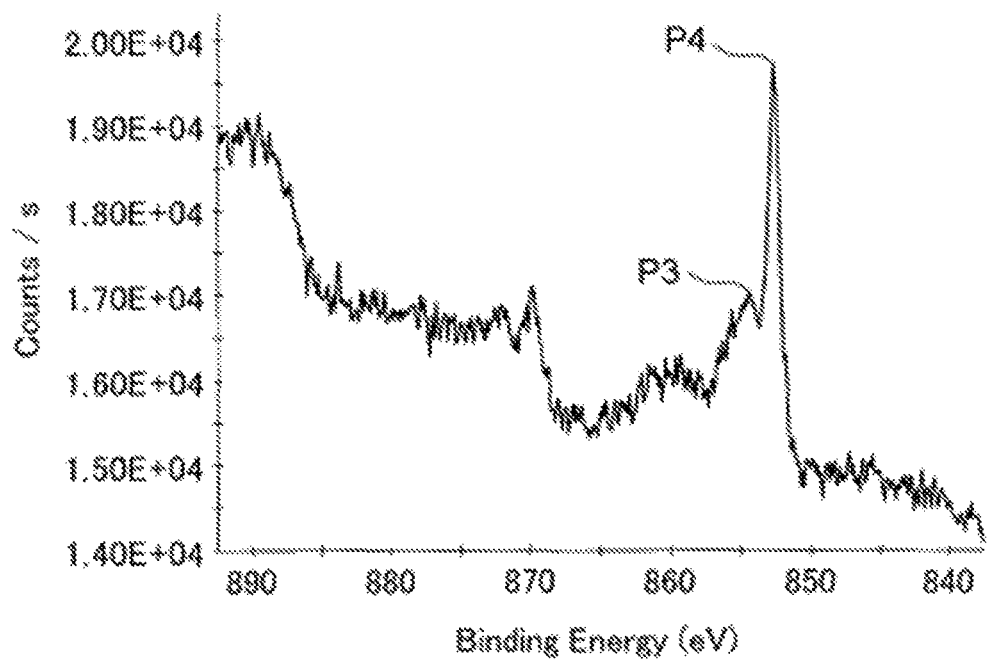
Figure 25A:
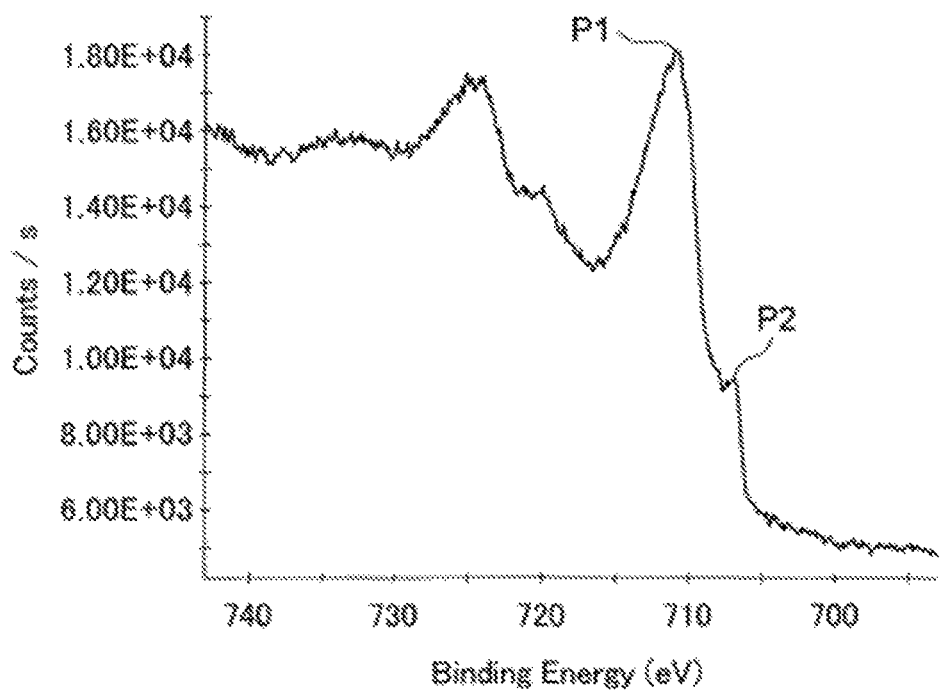
FIGS. 25(a) and 25(b) are views each showing a result of analyzing a third specimen cut out from a third winding body, by using the XPS apparatus.
Figure 25B:
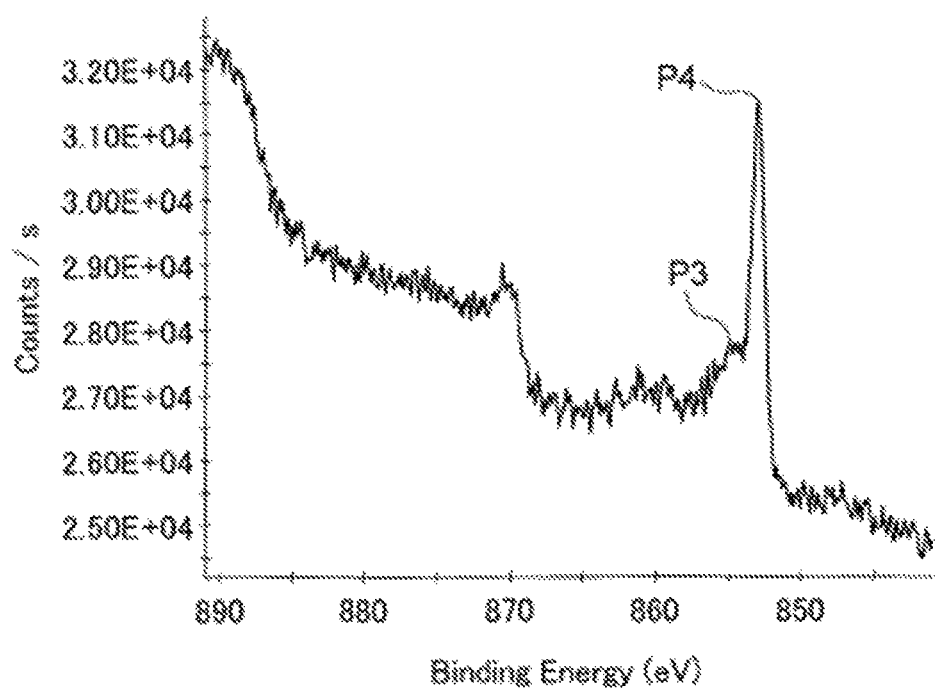
Figure 26A:
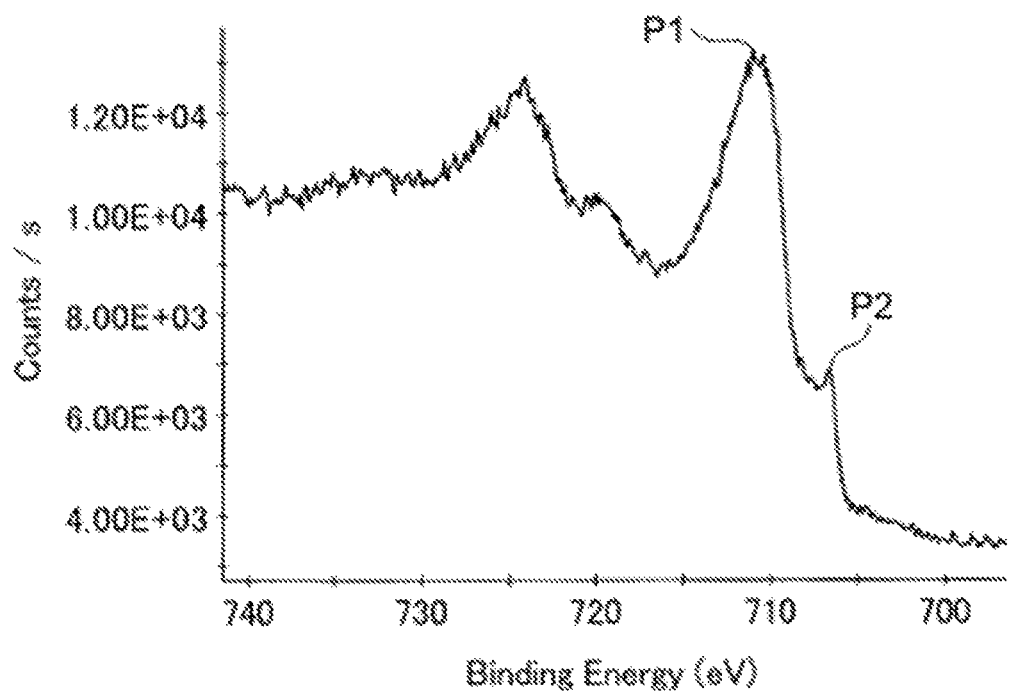
FIGS. 26(a) and 26(b) are views each showing a result of analyzing a fourth specimen cut out from a fourth winding body, by using the XPS apparatus.
Figure 26B:
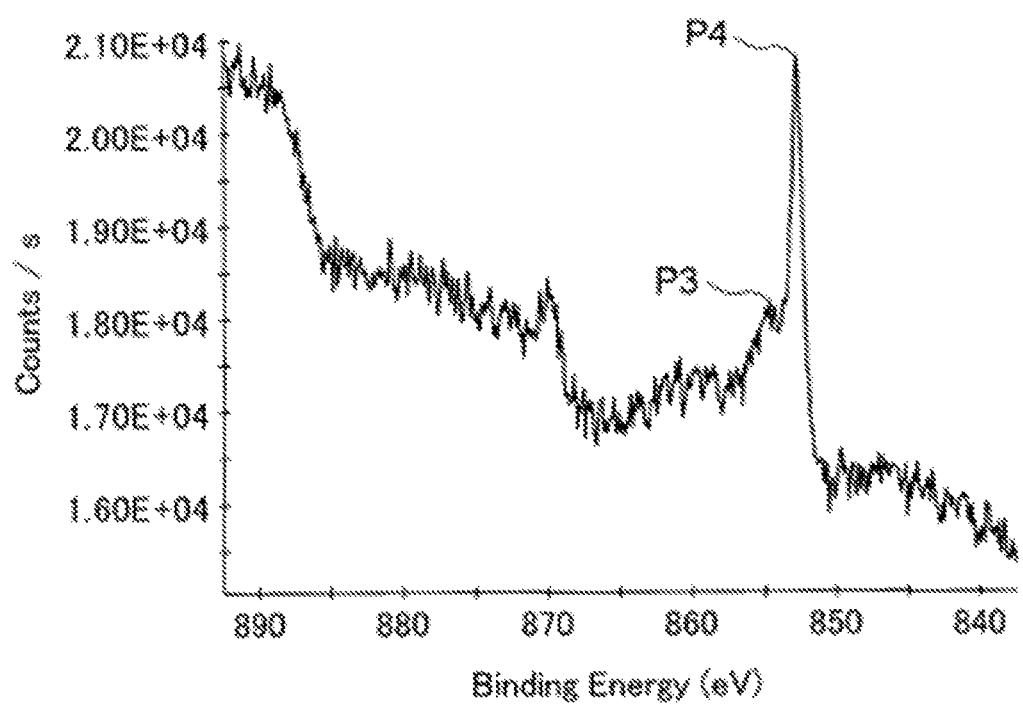

The aforementioned elongated metal plate of the first winding body was cut out by using a shear into a range of 200×200 mm, so as to obtain a first sample. Then, a dry film including a photosensitive layer having a thickness of 10 μm was attached to a surface of the first sample so as to provide a resist film on the surface of the first sample. After that, the resist film was exposed such that a grid-like resist pattern having a width w was formed, as shown in FIG. 23. The width w was set at 100 μm. Then, the first sample was immersed into a developing solution, and a time up to which the resist pattern having the width of 100 μm peeled off from the first sample was measured. As the developing solution, a solution having a concentration of 5.0 g/L of sodium carbonate manufactured by Soda Ash Japan Co., Ltd. was used. A temperature of the developing solution was set at 24° C.

In this example, when it took the resist pattern immersed in the developing solution 15 minutes or more to peel off, it was evaluated that the adhesion property was satisfactory. On the other hand, when it took the resist pattern immersed in the developing solution less than 15 minutes to peel off, it was evaluated that the adhesion property was unsatisfactory. In this example, it took the resist pattern 13 minutes to peel off from the first sample. Thus, it can be said that the adhesion property between the first winding body from which the first specimen was cut out and the resist pattern is unsatisfactory.

Whether the resist pattern peels off from the metal plate or not can be judged based the fact whether the resist pattern has a curved portion or not, when the resist pattern is seen along the normal direction of the first surface of the metal plate. This is because, in the developing solution, a portion of the resist pattern, which peels off from the metal plate, floats to deform. FIG. 27 shows an example of a schematic diagram of the metal plate and the resist pattern in which a portion of the grid-like resist pattern peels off from the metal plate in the developing solution.

(Second to Fourth Winding Bodies)

Similarly to the first winding body, a second winding body to a fourth winding body around which an elongated metal plate having a thickness of 20 μm was wound were manufactured, by using a base metal made of an iron alloy containing 34 to 38 mass % of nickel, less than 0.1 mass % of chrome, balancing iron and unavoidable impurities. Further, similarly to the first winding body, the second winding body to the fourth winding body were subjected to the composition analysis and the evaluation on adhesion property to the resist pattern. FIGS. 24(a) and 24(b), FIGS. 25(a) and 25(b) and FIGS. 26(a) and 26(b) show the respective results of specimens cut out from the second winding body, the third winding body and the fourth winding body, which were analyzed by means of the aforementioned XPS apparatus.

(Summary of Evaluation Results of First to Fourth Winding Bodies)

Table 3 shows the peak planar dimension values of the aforementioned respective peaks P1 to P4, which were obtained by analyzing the specimens taken out from the elongated metal plates of the first winding body to the fourth winding body. In addition, Table 3 shows the calculated results of A1/A2, where A1 is a sum of a peak planar dimension value of nickel oxide and a peak planar dimension value of nickel hydroxide, and A2 is a sum of a peak planar dimension value of iron oxide and a peak planar dimension value of iron hydroxide. As shown in Table 3, the first winding body and the second winding body did not satisfy the aforementioned condition (1). On the other hand, the third winding body and the fourth winding body satisfied the aforementioned condition (1). For the purpose of reference, Table 4 shows the compositions of the elongated metal plates of the first winding body to the fourth winding body, which were calculated by the composition analysis using the XPS method.

TABLE 3

|  | Peak P1 | Peak P2 | Peak P3 | Peak P4 | A1/A2 |
|---|---|---|---|---|---|
| First Winding Body | 22329.3 | 4481.8 | 9090.5 | 4748.9 | 0.41 |
| Second Winding Body | 45167.9 | 8984.6 | 20021.6 | 7849.8 | 0.44 |
| Third Winding Body | 36717.5 | 5195.9 | 8444.0 | 6138.4 | 0.23 |
| Forth Winding Body | 27134.2 | 3991.4 | 7948.8 | 4690.9 | 0.29 |

TABLE 4

|  | Composition (at %) | | | | |
|---|---|---|---|---|---|
|  | C | N | O | Fe | Ni |
| First Winding Body | 12.7 | 1.0 | 46.5 | 32.1 | 7.7 |
| Second Winding Body | 15.6 | 0.8 | 47.4 | 29.5 | 6.7 |
| Third Winding Body | 32.7 | 0.8 | 40.4 | 22.2 | 4.0 |
| Forth Winding Body | 18.4 | 1.2 | 45.9 | 28.5 | 6.1 |

(Summary of Evaluation Results on Adhesion Property to Resist Pattern)

Table 5 shows results of evaluation of the adhesion property to the resist pattern, which was performed to the samples cut out from the elongated metal plates of the first winding body to the fourth winding body. In the column "Adhesion Property" of Table 5, "Satisfactory" means that it took the resist pattern immersed in the developing solution 15 minutes or more to peel off from the resist pattern, and "Unsatisfactory" means that it took the resist pattern immersed in the developing solution less than 15 minutes to peel off from the resist pattern.

TABLE 5

|  | Peeling Time | Adhesion Property |
|---|---|---|
| First Winding Body | 13 | Unsatisfactory |
| Second Winding Body | 14 | Unsatisfactory |
| Third Winding Body | 35 | Satisfactory |
| Forth Winding Body | 33 | Satisfactory |

As shown in Table 3 and Table 5, the samples cut out from the third winding body and the fourth winding body had a satisfactory adhesion property to the resist pattern. On the other hand, the samples cut out from the first winding body and the second winding body did not have a sufficient adhesion property to the resist pattern. From these results, it can be said that it is effective that, in the surface of the metal plate, a ratio of nickel oxide and nickel hydroxide relative to iron oxide and iron hydroxide is decreased, to be more specific, the aforementioned A1/A2 is made less than 0.4, in order to ensure the adhesion property to the resist pattern.

(Fifth to Ninth Winding Bodies)

Similarly to the first winding body, a fifth to eighth winding body around which an elongated metal plate having a thickness of 20 μm was wound, and a ninth winding body around which an elongated metal plate having a thickness of 18 μm was wound were manufactured, by using a base metal made of an iron alloy containing 34 to 38 mass % of nickel, less than 0.1 mass % of chrome, balancing iron and unavoidable impurities. Further, similarly to the first winding body, the fifth winding body to the ninth winding body were subjected to the composition analysis and the evaluation on adhesion property to the resist pattern.

(Summary of Evaluation Results of First to Fourth Winding Bodies)

Table 6 shows the peak planar dimension values of the aforementioned respective peaks P1 to P4, which were obtained by analyzing the specimens taken out from the elongated metal plates of the fifth winding body to the ninth winding body. In addition, Table 6 shows the calculated results of A1/A2. As shown in Table 6, the sixth winding body did not satisfy the aforementioned condition (1). On the other hand, the fifth winding body and the seventh winding body to the ninth winding body satisfied the aforementioned condition (1). For the purpose of reference, Table 7 shows compositions of the elongated metal plates of the fifth winding body to the ninth winding body, which were calculated by the composition analysis using the XPS method.

TABLE 6

|  | Peak P1 | Peak P2 | Peak P3 | Peak P4 | A1/A2 |
|---|---|---|---|---|---|
| Fifth Winding Body | 24528.3 | 3176.6 | 9165.0 | 4292.1 | 0.37 |
| Sixth Winding Body | 28969.1 | 5527.5 | 13102.1 | 5083.0 | 0.45 |
| Seventh Winding Body | 33256.9 | 1043.7 | 6615.7 | 2013.6 | 0.20 |
| Eighth Winding Body | 30606.3 | 3739.6 | 8098.6 | 6506.4 | 0.26 |
| Ninth Winding Body | 97247.0 | 6789.0 | 19847.0 | 12266.0 | 0.20 |

TABLE 7

|  | Composition (at %) | | | | |
|---|---|---|---|---|---|
|  | C | N | O | Fe | Ni |
| Fifth Winding Body | 16.2 | 1.0 | 45.1 | 30.6 | 7.1 |
| Sixth Winding Body | 33.3 | 2.1 | 41.6 | 18.4 | 4.7 |
| Seventh Winding Body | 24.6 | 0.8 | 47.7 | 24.2 | 2.7 |
| Eighth Winding Body | 25.9 | 0.6 | 42.0 | 27.0 | 4.6 |
| Ninth Winding Body | 34.6 | 1.3 | 42.6 | 17.4 | 4.1 |

(Summary of Evaluation Results on Adhesion Property to Resist Pattern)

Table 8 shows results of evaluation of the adhesion property to the resist pattern, which was performed to the samples cut out from the elongated metal plates of the fifth winding body to the ninth winding body.

TABLE 8

|  | Adhesion Property |
|---|---|
| Fifth Winding Body | Satisfactory |
| Sixth Winding Body | Unsatisfactory |
| Seventh Winding Body | Satisfactory |
| Eighth Winding Body | Satisfactory |
| Ninth Winding Body | Satisfactory |

As shown in Table 6 and Table 8, the samples cut out from the fifth winding body and the seventh winding body to the ninth winding body had a satisfactory adhesion property to the resist pattern. On the other hand, the sample cut out from the sixth winding body did not have a sufficient adhesion property to the resist pattern. From these results, it can be said that it is effective that the aforementioned A1/A2 is made less than 0.4, in order to ensure the adhesion property to the resist pattern. Namely, the aforementioned condition (1) is a powerful judgment method for selecting a metal plate.

DESCRIPTION OF SYMBOLS

20 Deposition mask
21 Metal plate
21a First surface of metal plate
21b Second surface of metal plate
22 Effective area
23 Peripheral area
25 Through-hole
30 First recess
31 Wall surface
35 Second recess
36 Wall surface
43 Top portion
64 Elongated metal plate
64a First surface of elongated metal plate
64b Second surface of elongated metal plate
65a First resist pattern
65b Second resist pattern
65c First resist film
65d Second resist film
81 Irradiation unit
82 Detection unit
98 Deposition material

The invention claimed is:

1. A manufacturing method for a metal plate used for manufacturing a deposition mask having a plurality of through-holes formed therein, the method comprising a preparation step of preparing a plate member made of an iron alloy containing nickel,
wherein:
when a composition analysis of a first surface of the metal plate obtained from the plate member is performed by using an X-ray photoelectron spectroscopy, a ratio A1/A2 obtained by the result of the X-ray photoelectron spectroscopy is 0.4 or less, where A1 is a sum of a peak planar dimension value of nickel oxide and a peak planar dimension value of nickel hydroxide, and A2 is a sum of a peak planar dimension value of iron oxide and a peak planar dimension value of iron hydroxide; and
in the composition analysis of the first surface of the metal plate by means of the X-ray photoelectron spectroscopy, an incident angle of an X-ray emitted to the metal plate on the first surface is 45 degrees, and an acceptance angle of photoelectrons discharged from the metal plate is 90 degrees.

2. The manufacturing method for a metal plate according to claim 1, further comprising an annealing step of annealing the plate member to obtain the metal plate.

3. The manufacturing method for a metal plate according to claim 2, the plate member is annealed in the annealing step so that the ratio A1/A2 is 0.4 or less.

4. The manufacturing method for a metal plate according to claim 2, wherein
the annealing step is performed in an irreducible atmosphere or an inert gas atmosphere.

5. The manufacturing method for a metal plate according to claim 2, wherein
the annealing step is performed in an inert gas atmosphere including nitrogen gas.

6. The manufacturing method for a metal plate according to claim 1, wherein
the preparation step includes a rolling step of rolling a base metal made of an iron alloy containing nickel.

7. The manufacturing method for a metal plate according to claim 1, wherein
the preparation step includes a foil creating step of creating a plating film by using a plating liquid including a solution containing a nickel compound and a solution containing an iron compound.

8. The manufacturing method for a metal plate according to claim 1, wherein
a thickness of the metal plate is 85 µm or less.

9. The manufacturing method for a metal plate according to claim 1, wherein
a thickness of the metal plate is 20 µm or less.

10. The manufacturing method for a metal plate according to claim 1, wherein
the ratio A1/A2 is 0.3 or less.

11. The manufacturing method for a metal plate according to claim 1, wherein
the metal plate obtained by the plate member is for manufacturing the deposition mask by exposing and developing a dry film attached to the first surface of the metal plate to form a first resist pattern, and by etching an area of the first surface of the metal plate to form the plurality of through-holes, the area being not covered with the first resist pattern.

* * * * *